(12) United States Patent
Lang

(10) Patent No.: US 7,166,427 B1
(45) Date of Patent: Jan. 23, 2007

(54) DETECTING THE EXPRESSION OF THE DESC1 GENE IN SQUAMOUS CELL CARCINOMA

(75) Inventor: Jas C. Lang, Worthington, OH (US)

(73) Assignee: The Ohio University Research Foundation, Columbus, OH (US)

( * ) Notice: Subject to any disclaimer, the term of this patent is extended or adjusted under 35 U.S.C. 154(b) by 0 days.

(21) Appl. No.: 09/674,035

(22) PCT Filed: Nov. 11, 1999

(86) PCT No.: PCT/IB99/01818

§ 371 (c)(1),
(2), (4) Date: Dec. 11, 2000

(87) PCT Pub. No.: WO00/50061

PCT Pub. Date: Aug. 31, 2000

Related U.S. Application Data

(60) Provisional application No. 60/122,747, filed on Feb. 26, 1999.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.31

(58) Field of Classification Search .................... 435/6; 536/23.1, 24.31
See application file for complete search history.

(56) References Cited

U.S. PATENT DOCUMENTS

2003/0073129 A1 * 4/2003 Baker et al.

FOREIGN PATENT DOCUMENTS

WO         00/12708       3/2000

OTHER PUBLICATIONS

Reiger et al. (Glossary of Genetics and Cytogenetics, Classical and Molecular, 4th Ed., Springer-Verlay, Berlin, 1976.*
Genes IV (Lewin et al, Oxford University Press, p. 810, 1990.*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987.*
Lin et al Biochemistry USA vol. 14:1559-1563 (1975.*
The 1991 Boehringer Mannheim Biochemical Catalog, p. 557.*
Abstract No. 344, "Gene Alterations in Squamous Cell Carcinoma of the Head and Neck" by Lang, et al. *International Journal of Molecular Medicine*, vol. 6, Supplement 1, Proceedings of the Abstracts of the 5 World Congress on Advances in Oncology and 3rd International Symposium on Molecular Medicine, Oct. 19-21, 2000, Hersonissos, Crete, Greece.
Abstract No. 194, "Isolation of Differently Expressed Genes in Squamous Cell Carcinoma of the Head and Neck" by Lang, et al., 5th International Conference on Head and Neck Cancer, Jul. 29-Aug. 2, 2000, San Francisco, California.
Abstract No. 30, "Differential Expression of a Novel Serine Protease-Like Gene in Squamous Cell Carcinoma of the Head and Neck" by Lang, et al., The Ohio State University Comprehensive Cancer Center Scientific Retreat, Cherry Valley Lodge, Newark, Ohio, Dec. 16, 1999.
Genbank Accession No. NM_041058, Nov. 2, 2000.
Genbank Accession No. AF064819, Oct 3, 2000.

* cited by examiner

*Primary Examiner*—Jeffrey Siew
*Assistant Examiner*—Sean E Aeder
(74) *Attorney, Agent, or Firm*—Calfee, Halter & Griswold LLP

(57) ABSTRACT

The present invention provides a novel method for diagnosing squamous cell carcinoma or prostate cancer in a tissue sample. The method does not involve visual examination of morphology. The method comprises providing a sample from the subject and assaying for the presence, or absence or reduced level of expression of a novel gene, hereinafter referred to as the "DESC1 gene". The method comprises isolating RNA, preferably mRNA from tissue samples, and detecting the mRNA which encodes all or part of DESC1 protein. Preferably the detection comprises amplifying the mRNA, preferably by reverse transcriptase-PCR using primers specific to a region in the DESC1 gene; and detecting the presence or absence of the amplified product to determine whether DESC1 mRNA is present or absent in the tissue sample. Alternatively the detection comprises separating the RNA which encodes all or part of DESC1 protein from the total RNA, preferably by separating on an agarose gel, and detecting the mRNA encoding DESC1, preferably by using a probe specific for such mRNA. Optionally, the DESC1 mRNA when present, is also quantified using conventional techniques. The present invention also relates to polynucleotides which encode the DESC1 protein, to the DESC1 protein, and to antibodies to the DESC1 protein. The present invention also relates to hybridization probes, and to primers useful in the method of detecting DESC1 mRNA.

5 Claims, 10 Drawing Sheets

Fig. 1A

```
   1   tgacttggatgtagacctcgaccttcacaggactcttcattgctggttggcaatg ATG TAT CGG CCA GAT GTG    73
   1                                                            M   Y   R   P   D   V     6

74   GTG AGG GCT AGG AAA AGA GTT TGT TGG GAA CCC TGG GTT ATC GGC CTC GTC ATC TTC ATA   133
   7    V   R   A   R   K   R   V   C   W   E   P   W   V   I   G   L   V   I   F   I    26

134   TCC CTG ATT GTC CTG GCA GTG TGC ATT GGA CTC ACT GTT CAT TAT GTG AGA TAT AAT CAA   193
  27    S   L   I   V   L   A   V   C   I   G   L   T   V   H   Y   V   R   Y   N   Q    46

194   AAG AAG ACC TAC AAT TAC TAT AGC ACA TTG TCA TTT ACA ACT GAC AAA CTA TAT GCT GAG   253
  47    K   K   T   Y   N   Y   Y   S   T   L   S   F   T   T   D   K   L   Y   A   E    66

254   TTT GGC AGA GAG GCT TCT AAC AAT TTT ACA GAA ATG AGC CAG AGA CTT GAA TCA ATG GTG   313
  67    F   G   R   E   A   S   N   N   F   T   E   M   S   Q   R   L   E   S   M   V    86

314   AAA AAT GCA TTT TAT AAA TCT CCA TTA AGG GAA GAA TTT GTC AAG TCT CAG GTT ATC AAG   373
  87    K   N   A   F   Y   K   S   P   L   R   E   E   F   V   K   S   Q   V   I   K   106

374   TTC AGT CAA CAG AAG CAT GGA GTG TTG GCT CAT ATG CTG TTG ATT TGT AGA TTT CAC TCT   433
 107    F   S   Q   Q   K   H   G   V   L   A   H   M   L   L   I   C   R   F   H   S   126

434   ACT GAG GAT CCT GAA ACT GTA GAT AAA ATT GTT CAA CTT GTT TTA CAT GAA AAG CTG CAA   493
 127    T   E   D   P   E   T   V   D   K   I   V   Q   L   V   L   H   E   K   L   Q   146

494   GAT GCT GTA GGA CCC CCT AAA GTA GAT CCT CAC TCA GTT AAA ATT AAA AAA ATC AAC AAG   553
 147    D   A   V   G   P   P   K   V   D   P   H   S   V   K   I   K   K   I   N   K   166

554   ACA GAA ACA GAC AGC TAT CTA AAC CAT TGC TGC GGA ACA CGA AGA AGT AAA ACT CTA GGT   613
 167    T   E   T   D   S   Y   L   N   H   C   C   G   T   R   R   S   K   T   L   G   186

614   CAG AGT CTC AGG ATC GTT GGT GGG ACA GAA GTA GAA GAG GGT GAA TGG CCC TGG CAG GCT   673
 187    Q   S   L   R   I   V   G   G   T   E   V   E   E   G   E   W   P   W   Q   A   206

674   AGC CTG CAG TGG GAT GGG AGT CAT CGC TGT GGA GCA ACC TTA ATT AAT GCC ACA TGG CTT   733
 207    S   L   Q   W   D   G   S   H   R   C   G   A   T   L   I   N   A   T   W   L   226

734   GTG AGT GCT GCT CAC TGT TTT ACA ACA TAT AAG AAC CCT GCC AGA TGG ACT GCT TCC TTT   793
 227    V   S   A   A   H   C   F   T   T   Y   K   N   P   A   R   W   T   A   S   F   246

794   GGA GTA ACA ATA AAA CCT TCG AAA ATG AAA CGG GGT CTC CGG AGA ATA ATT GTC CAT GAA   853
 247    G   V   T   I   K   P   S   K   M   K   R   G   L   R   R   I   I   V   H   E   266

854   AAA TAC AAA CAC CCA TCA CAT GAC TAT GAT ATT TCT CTT GCA GAG CTT TCT AGC CCT GTT   913
 267    K   Y   K   H   P   S   H   D   Y   D   I   S   L   A   E   L   S   S   P   V   286

914   CCC TAC ACA AAT GCA GTA CAT AGA GTT TGT CTC CCT GAT GCA TCC TAT GAG TTT CAA CCA   973
 287    P   Y   T   N   A   V   H   R   V   C   L   P   D   A   S   Y   E   F   Q   P   306

974   GGT GAT GTG ATG TTT GTG ACA GGA TTT GGA GCA CTG AAA AAT GAT GGT TAC AGT CAA AAT  1033
 307    G   D   V   M   F   V   T   G   F   G   A   L   K   N   D   G   Y   S   Q   N   326

1034   CAT CTT CGA CAA GCA CAG GTG ACT CTC ATA GAC GCT ACA ACT TGC AAT GAA CCT CAA GCT  1093
 327    H   L   R   Q   A   Q   V   T   L   I   D   A   T   T   C   N   E   P   Q   A   346

1094   TAC AAT GAC GCC ATA ACT CCT AGA ATG TTA TGT GCT GGC TCC TTA GAA GGA AAA ACA GAT  1153
 347    Y   N   D   A   I   T   P   R   M   L   C   A   G   S   L   E   G   K   T   D   366

1154   GCA TGC CAG GGT GAC TCT GGA GGA CCA CTG GTT AGT TCA GAT GCT AGA GAT ATC TGG TAC  1213
 367    A   C   Q   G   D   S   G   G   P   L   V   S   S   D   A   R   D   I   W   Y   386

1214   CTT GCT GGA ATA GTG AGC TGG GGA GAT GAA TGT GCG AAA CCC AAC AAG CCT GGT GTT TAT  1273
 387    L   A   G   I   V   S   W   G   D   E   C   A   K   P   N   K   P   G   V   Y   406

1274   ACT AGA GTT ACG GCC TTG CGG GAC TGG ATT ACT TCA AAA ACT GGT ATC TAA gagagaaaagcc  1336
 407    T   R   V   T   A   L   R   D   W   I   T   S   K   T   G   I   *                423

1337   tcatggaacagataacatttttttttgtttttgggtgtggaggccattttagagatacagaattggagaagacttgca   1416

1417   aaacagctagatttgactgatctcaataaactgtttgcttgatgcaaaaaaaaaa                          1471
```

Fig. 1B

```
   1   tgacttggatgtagacctcgaccttcacaggactcttcattgctggttggcaatg ATG TAT CGG CCA GAT GTG    73
   1                                                            M   Y   R   P   D   V     6

74   GTG AGG GCT AGG AAA AGA GTT TGT TGG GAA CCC TGG GTT ATC GGC CTC GTC ATG TTC ATA   133
   7    V   R   A   R   K   R   V   C   W   E   P   W   V   I   G   L   V   M   F   I    26

134   TCC CTG ATT GTC CTG GCA GTG TGC ATT GGA GTC ACT GTT CAT TAT GTG AGA TAT AAT CAA   193
  27    S   L   I   V   L   A   V   C   I   G   V   T   V   H   Y   V   R   Y   N   Q    46

194   AAG AAG ACC TAC AAT TAC TAT AGC ACA TTG TCA TTT ACA ACT GAC AAA CTA TAT GCT GAG   253
  47    K   K   T   Y   N   Y   Y   S   T   L   S   F   T   T   D   K   L   Y   A   E    66

254   TTT GGC AGA GAG GCT TCT AAC AAT TTT ACA GAA ATG AGC CAG AGA CTT GAA TCA ATG GTG   313
  67    F   G   R   E   A   S   N   N   F   T   E   M   S   Q   R   L   E   S   M   V    86

314   AAA AAT GCA TTT TAT AAA TCT CCA TTA AGG GAA GAA TTT GTC AAG TCT CAG GTT ATC AAG   373
  87    K   N   A   F   Y   K   S   P   L   R   E   E   F   V   K   S   Q   V   I   K   106

374   TTC AGT CAA CAG AAG CAT GGA GTG TTG GCT CAT ATG CTG TTG ATT TGT AGA TTT CAC TCT   433
 107    F   S   Q   Q   K   H   G   V   L   A   H   M   L   L   I   C   R   F   H   S   126

434   ACT GAG GAT CCT GAA ACT GTA GAT AAA ATT GTT CAA CTT GTT TTA CAT GAA AAG CTG CAA   493
 127    T   E   D   P   E   T   V   D   K   I   V   Q   L   V   L   H   E   K   L   Q   146

494   GAT GCT GTA GGA CCC CCT AAA GTA GAT CCT CAC TCA GTT AAA ATT AAA AAA ATC AAC AAG   553
 147    D   A   V   G   P   P   K   V   D   P   H   S   V   K   I   K   K   I   N   K   166

554   ACA GAA ACA GAC AGC TAT CTA AAC CAT TGC TGC GGA ACA CGA AGA AGT AAA ACT CTA GGT   613
 167    T   E   T   D   S   Y   L   N   H   C   C   G   T   R   R   S   K   T   L   G   186

614   CAG AGT CTC AGG ATC GTT GGT GGG ACA GAA GTA GAA GAG GGT GAA TGG CCC TGG CAG GCT   673
 187    Q   S   L   R   I   V   G   G   T   E   V   E   E   G   E   W   P   W   Q   A   206

674   AGC CTG CAG TGG GAT GGG AGT CAT CGC TGT GGA GCA ACC TTA ATT AAT GCC ACA TGG CTT   733
 207    S   L   Q   W   D   G   S   H   R   C   G   A   T   L   I   N   A   T   W   L   226

734   GTG AGT GCT GCT CAC TGT TTT ACA ACA TAT AAG AAC CCT GCC AGA TGG ACT GCT TCC TTT   793
 227    V   S   A   A   H   C   F   T   T   Y   K   N   P   A   R   W   T   A   S   F   246

794   GGA GTA ACA ATA AAA CCT TCG AAA ATG AAA CGG GGT CTC CGG AGA ATA ATT GTC CAT GAA   853
 247    G   V   T   I   K   P   S   K   M   K   R   G   L   R   R   I   I   V   H   E   266

854   AAA TAC AAA CAC CCA TCA CAT GAC TAT GAT ATT TCT CTT GCA GAG CTT TCT AGC CCT GTT   913
 267    K   Y   K   H   P   S   H   D   Y   D   I   S   L   A   E   L   S   S   P   V   286

914   CCC TAC ACA AAT GCA GTA CAT AGA GTT TGT CTC CCT GAT GCA TCC TAT GAG TTT CAA CCA   973
 287    P   Y   T   N   A   V   H   R   V   C   L   P   D   A   S   Y   E   F   Q   P   306

974   GGT GAT GTG ATG TTT GTG ACA GGA TTT GGA GCA CTG AAA AAT GAT GGT TAC AGT CAA AAT  1033
 307    G   D   V   M   F   V   T   G   F   G   A   L   K   N   D   G   Y   S   Q   N   326

1034   CAT CTT CGA CAA GCA CAG GTG ACT CTC ATA GAC GCT ACA ACT TGC AAT GAA CCT CAA GCT  1093
 327    H   L   R   Q   A   Q   V   T   L   I   D   A   T   T   C   N   E   P   Q   A   346

1094   TAC AAT GAC GCC ATA ACT CCT AGA ATG TTA TGT GCT GGC TCC TTA GAA GGA AAA ACA GAT  1153
 347    Y   N   D   A   I   T   P   R   M   L   C   A   G   S   L   E   G   K   T   D   366

1154   GCA TGC CAG GGT GAC TCT GGA GGA CCA CTG GTT AGT TCA GAT GCT AGA GAT ATC TGG TAC  1213
 367    A   C   Q   G   D   S   G   G   P   L   V   S   S   D   A   R   D   I   W   Y   386

1214   CTT GCT GGA ATA GTG AGC TCG GGA GAT GAA TGT GCG AAA CCC AAC AAG CCT GGT GTT TAT  1273
 387    L   A   G   I   V   S   S   G   D   E   C   A   K   P   N   K   P   G   V   Y   406

1274   ACT AGA GTT ACG GCC TTG CGG GAC TGG ATT ACT TCA AAA ACT GGT ATC TAA gagagaaagcc  1336
 407    T   R   V   T   A   L   R   D   W   I   T   S   K   T   G   I   *                423

1337   tcatggaacagataacattttttttttgttttttgggtgtggaggccattttttagagatacagaattggagaagacttgca   1416

1417   aaacagctagatttgactgatctcaataaactgtttgcttgatgcaaaaaaaaa                              1471
```

Fig. 1B continued

```
   1 tgacttggatgtagacctcgaccttcacaggactcttcattgctggttggcaatg ATG TAT CGG CCA GAT GTG   73
   1                                                         M   Y   R   P   D   V    6

74 GTG AGG GCT AGG AAA AGA GTT TGT TGG GAA CCC TGG GTT ATC GGC CTC GTC ATG TTC ATA  133
   7  V   R   A   R   K   R   V   C   W   E   P   W   V   I   G   L   V   M   F   I   26

134 TCC CTG ATT GTC CTG GCA GTG TGC ATT GGA GTC ACT GTT CAT TAT GTG AGA TAT AAT CAA  193
  27  S   L   I   V   L   A   V   C   I   G   V   T   V   H   Y   V   R   Y   N   Q   46

194 AAG AAG ACC TAC AAT TAC TAT AGC ACA TTG TCA TTT ACA ACT GAC AAA CTA TAT GCT GAG  253
  47  K   K   T   Y   N   Y   Y   S   T   L   S   F   T   T   D   K   L   Y   A   E   66

254 TTT GGC AGA GAG GCT TCT AAC AAT TTT ACA GAA ATG AGC CAG AGA CTT GAA TCA ATG GTG  313
  67  F   G   R   E   A   S   N   N   F   T   E   M   S   Q   R   L   E   S   M   V   86

314 AAA AAT GCA TTT TAT AAA TCT CCA TTA AGG GAA GAA TTT GTC AAG TCT CAG GTT ATC AAG  373
  87  K   N   A   F   Y   K   S   P   L   R   E   E   F   V   K   S   Q   V   I   K  106

374 TTC AGT CAA CAG AAG CAT GGA GTG TTG GCT CAT ATG CTG TTG ATT TGT AGA TTT CAC TCT  433
 107  F   S   Q   Q   K   H   G   V   L   A   H   M   L   L   I   C   R   F   H   S  126

434 ACT GAG GAT CCT GAA ACT GTA GAT AAA ATT GTT CAA CTT GTT TTA CAT GAA AAG CTG CAA  493
 127  T   E   D   P   E   T   V   D   K   I   V   Q   L   V   L   H   E   K   L   Q  146

494 GAT GCT GTA GGA CCC CCT AAA GTA GAT CCT CAC TCA GTT AAA ATT AAA AAA ATC AAC AAG  553
 147  D   A   V   G   P   P   K   V   D   P   H   S   V   K   I   K   K   I   N   K  166

554 ACA GAA ACA GAC AGC TAT CTA AAC CAT TGC TGC GGA ACA CGA AGA AGT AAA ACT CTA GGT  613
 167  T   E   T   D   S   Y   L   N   H   C   C   G   T   R   R   S   K   T   L   G  186

614 CAG AGT CTC AGG ATC GTT GGT GGG ACA GAA GTA GAA GAG GGT GAA TGG CCC TGG CAG GCT  673
 187  Q   S   L   R   I   V   G   G   T   E   V   E   E   G   E   W   P   W   Q   A  206

674 AGC CTG CAG TGG GAT GGG AGT CAT CGC TGT GGA GCA ACC TTA ATT AAT GCC ACA TGG CTT  733
 207  S   L   Q   W   D   G   S   H   R   C   G   A   T   L   I   N   A   T   W   L  226

734 GTG AGT GCT GCT CAC TGT TTT ACA ACA TAT AAG AAC CCT GCC AGA TGG ACT GCT TCC TTT  793
 227  V   S   A   A   H   C   F   T   T   Y   K   N   P   A   R   W   T   A   S   F  246

794 GGA GTA ACA ATA AAA CCT TCG AAA ATG AAA CGG GGT CTC CGG AGA ATA ATT GTC CAT GAA  853
 247  G   V   T   I   K   P   S   K   M   K   R   G   L   R   R   I   I   V   H   E  266

854 AAA TAC AAA CAC CCA TCA CAT GAC TAT GAT ATT TCT CTT GCA GAG CTT TCT AGC CCT GTT  913
 267  K   Y   K   H   P   S   H   D   Y   D   I   S   L   A   E   L   S   S   P   V  286

914 CCC TAC ACA AAT GCA GTA CAT AGA GTT TGT CTC CCT GAT GCA TCC TAT GAG TTT CAA CCA  973
 287  P   Y   T   N   A   V   H   R   V   C   L   P   D   A   S   Y   E   F   Q   P  306

974 GGT GAT GTG ATG TTT GTG ACA GGA TTT GGA GCA CTG AAA AAT GAT GGT TAC AGT CAA AAT 1033
 307  G   D   V   M   F   V   T   G   F   G   A   L   K   N   D   G   Y   S   Q   N  326

1034 CAT CTT CGA CAA GCA CAG GTG ACT CTC ATA GAC GCT ACA ACT TGC AAT GAA CCT CAA GCT 1093
 327  H   L   R   Q   A   Q   V   T   L   I   D   A   T   T   C   N   E   P   Q   A  346

1094 TAC AAT GAC GCC ATA ACT CCT AGA ATG TTA TGT GCT GGC TCC TTA GAA GGA AAA ACA GAT 1153
 347  Y   N   D   A   I   T   P   R   M   L   C   A   G   S   L   E   G   K   T   D  366

1154 GCA TGC CAG GGT GAC TCT GGA GGA CCA CTG GTT AGT TCA GAT GCT AGA GAT ATC TGG TAC 1213
 367  A   C   Q   G   D   S   G   G   P   L   V   S   S   D   A   R   D   I   W   Y  386

1214 CTT GCT GGA ATA GTG AGC TCG GGA GAT GAA TGT GCG AAA CCC AAC AAG CCT GGT GTT TAT 1273
 387  L   A   G   I   V   S   S   G   D   E   C   A   K   P   N   K   P   G   V   Y  406

1274 ACT AGA GTT ACG GCC TTG CGG GAC TGG ATT ACT TCA AAA ACT GGT ATC TAA gagagaaagcc 1336
 407  T   R   V   T   A   L   R   D   W   I   T   S   K   T   G   I   *              423

1337 tcatggaacagataacatttttttttgtttttgggtgtggaggccatttttagagatacagaattggagaagacttgca 1416

1417 aaacagctagatttgactgatctcaataaactgtttgcttgatgcaaaaaaaaa                           1471
```

DETECTING THE EXPRESSION OF THE DESC1 GENE IN SQUAMOUS CELL CARCINOMA

CROSS-REFERENCE TO RELATED APPLICATIONS

This application is a continuation of copending International Application PCT/IB99/01818, filed on Nov. 11, 1999 and which designated the U.S. The non-provisional application designated above, namely International Application PCT/IB99/01818, filed Nov. 11, 1999, claims priority from U.S. Provisional Application 60/122,747, filed Feb. 26, 1999.

This invention was made in part with government support under CA63134 and DE12704 awarded by the National Institutes of Health. The U.S. government has certain rights in the invention.

BACKGROUND OF THE INVENTION

Typically, morphological examination of the tissues is performed to characterize squamous cell carcinomas of the head and neck and tissues adjacent to such tumor tissue. The morphological examination usually involves the sectioning and staining of an excised tissue sample followed by microscopic examination by a cytologist or pathologist. However, visual examination does result in some errors, particularly by pathologists who do not routinely encounter such tissue samples.

Accordingly, it is desirable to have a technique which does not require visual examination of morphological characteristics to diagnose or confirm a pathologist's diagnosis of squamous cell carcinoma of the head and neck.

SUMMARY OF THE INVENTION

The present invention provides a novel method for diagnosing squamous cell carcinoma or prostate cancer in a tissue sample. The method does not involve visual examination of morphology. The method comprises providing a sample from the subject and assaying for the presence, or absence or reduced level of expression of a novel gene, hereinafter referred to as the "DESC1 gene". The method comprises isolating RNA, preferably mRNA from tissue samples, and detecting the mRNA which encodes all or part of DESC1 protein. Preferably the detection comprises amplifying the mRNA, preferably by reverse transcriptase-PCR using primers specific to a region in the DESC1 gene; and detecting the presence or absence of the amplified product to determine whether DESC1 mRNA is present or absent in the tissue sample. Alternatively the detection comprises separating the RNA which encodes all or part of DESC1 protein from the total RNA, preferably by separating on an agarose gel, and detecting the mRNA encoding DESC1, preferably by using a probe specific for such mRNA. Optionally, the DESC1 mRNA when present, is also quantified using conventional techniques.

The present invention also relates to polynucleotides which encode the DESC1 protein, to the DESC1 protein, and to antibodies to the DESC1 protein. The present invention also relates to hybridization probes, and to primers useful in the method of detecting DESC1 mRNA.

BRIEF DESCRIPTION OF THE FIGURES

FIG. 1A is the nucleotide sequence, SEQ.ID.NO. 1, of a cDNA which encodes a DESC1 protein, with the predicted amino acid sequence of the amino acid sequence, SEQ. ID. NO. 2 encoded by the nucleotide sequence. Putative initiation and termination codons are boxed, as are residues predicted to represent conserved amino acids of the catalytic triad. Suggested location of catalytic cleavage site is shown by vertical arrow. Consensus polyadenylation signals are double underlined. The predicted hydrophobic transmembrane sequence or signal peptide is located at about amino acids 18–37 and is underlined.

FIG. 1B is an alternate nucleotide sequence, SEQ.ID.NO. 3, of a cDNA which encodes a DESC1 protein, with the predicted amino acid sequence of the amino acid sequence, SEQ. ID. NO. 4 encoded by the nucleotide sequence.

DETAILED DESCRIPTION OF THE INVENTION

Figure 2:
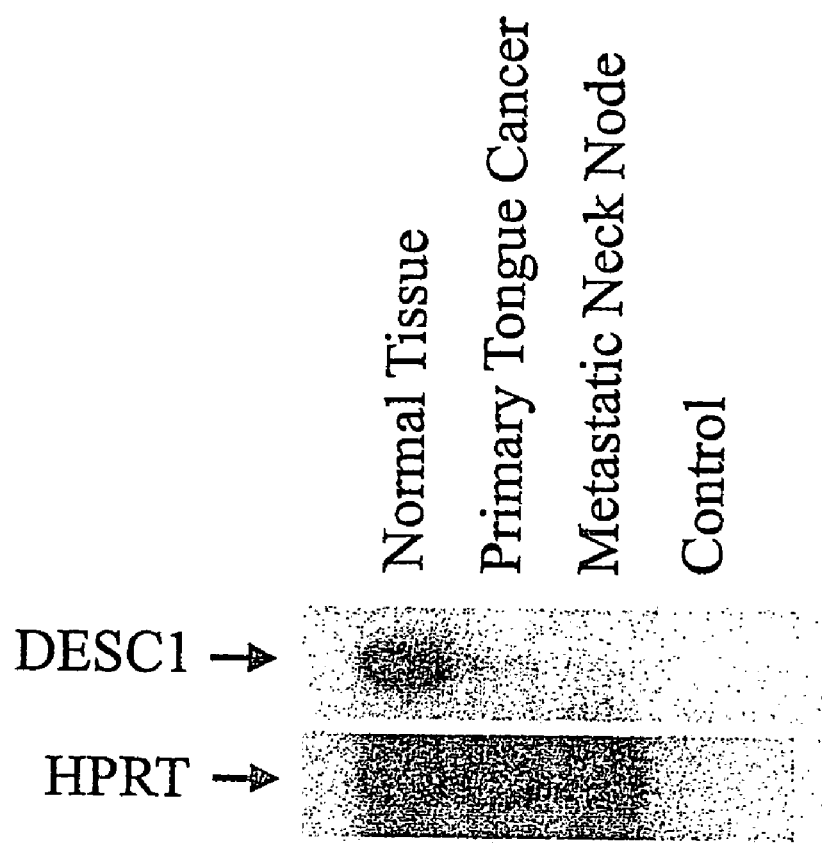
FIG. 2. DESC1 expression in normal tissue and metastatic neck node used for RDA analysis and in primary carcinoma from the same patient. RT-PCR analysis. Primers utilized: D10, D11. Size of RT-PCR product, 555 bp.

A novel gene has been discovered which is expressed in significant levels in epithelial derived tissues, specifically epithelial tissues of the head, neck, oral mucosa, tonsils, prostate, testes, and skin in healthy individuals, i.e. individuals who do not have squamous cell carcinoma or prostate carcinoma. However, in tumor tissue samples taken from patients with squamous cell carcinoma, particularly of the head and neck, the expression of the DESC1 gene is absent or significantly reduced. The differential expression permits the identification of squamous cell carcinoma of the head and neck.

Similarly, expression of the DESC1 gene is reduced or absent in prostate carcinoma and, thus, permits identification of prostate carcinoma.

Polynucleotides

The present invention provides isolated polynucleotides which encode a DESC1 protein. One embodiment of a polynucleotide which encodes a DESC1 protein is shown in FIG. 1A, another embodiment is shown in FIG. 1B Due to the known degeneracy of the genetic code wherein more than one codon can encode the same amino acid, a DNA sequence may vary from that shown in FIG. 1A and still encode a DESC1 protein having the amino acid sequences shown in FIG. 1A. Similarly, a DNA sequence may vary from that shown in FIGS. 1A and 1B and still encode the amino acid sequence shown in FIG. 1B.

The present invention also encompasses polynucleotides having sequences that are capable of hybridizing to the nucleotide sequences of FIGS. 1A and 1B under stringent conditions, preferably highly stringent conditions. Hybridization conditions are based on the melting temperature TM of the nucleic acid binding complex or probe, as described in Berger and Kimmel (1987) Guide to Molecular Cloning Techniques, Methods in Enzymology, Vol. 152, Academic Press. The term "stringent conditions, as used herein, is the "stringency" which occurs within a range from about Tm-5 (5° below the melting temperature of the probe) to about 20° C. below Tm. "Highly Stringent hybridization conditions" refers to an overnight incubation at 42 degree C. in a solution comprising 50% formamide, 5×SSC (750 mM NaCl, 75 mM sodium citrate), 50 mM sodium phosphate (pH 7.6), 5× Denhardt's solution, 10% dextran sulfate, and 20 µg/ml denatured, sheared salmon sperm DNA, followed by washing the filters in 0.2×SSC at about 65 degree C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Changes in the stringency of hybridization and signal detection are primarily accomplished through the manipulation of formamide concentration (lower percentages of formamide result in lower stringency); salt conditions, or temperature. For example, moderately high stringency conditions include an overnight incubation at 37 degree C. in a solution comprising 6×SSPE (20×SSPE 3M NaCl; 0.2 M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The present invention also encompasses alleles of the DESC1 protein encoding sequences. As used herein, the term an "allele" or "allelic sequence" is an alternative form of an DESC1 encoding sequence. The allele may result from one or more mutations in the DESC1 encoding sequence. Such mutations typically arise from natural addition, deletion of substitution of nucleotides in the open reading frame sequences. Any gene which encodes a DESC1 protein may have none, one, or several allelic forms. Such alleles are identified using conventional techniques, such as, for example, screening libraries with probes.

The present invention also encompasses altered polynucleotides which encode a DESC1 protein. Such alterations include deletions, additions, or substitution is. Such alterations may produce a silent change and result in a DESC1 protein having the same amino acid sequence as the DESC1 protein encoded by the unaltered polynucleotide. Such alterations may produce a nucleotide sequence possessing non-naturally occurring codons. For example, codons preferred by a particular prokaryotic or eucaryotic host may be incorporated into the nucleotide sequences shown in FIGS. 1A and 1B to increase the rate of expression of the polypeptides encoded by such sequences. Such alterations, conventionally, are accomplished using site-directed mutagenesis.

The polynucleotides are useful for producing DESC1 protein. For example, an RNA molecule encoding a DESC1 protein is used in a cell-free translation systems to prepare such polypeptide. Alternatively, a DNA molecule encoding a DESC1 protein is introduced into an expression vector and used to transform cells. Examples of expression vectors are chromosomal, nonchromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovinis, fowl pox virus, pseudorabies, baculovirus, and retrovirus. The DNA sequence is introduced into the expression vector by conventional procedures.

Accordingly, the present invention also relates to recombinant constructs comprising one of more of the polynucleotide sequences. Examples of constricts are vectors, such as a plasmid, phagemid, or viral vector, into which a sequence that encodes the DESC1 protein has been inserted. In the expression vector, the DNA sequence which en-codes the DESC1 protein is operatively linked to an expression control sequence, i.e., a promoter, which directs in RNA synthesis. Representative examples of such promoters, include the LTR or SV40 promoter, the *E. coli* lac or tip, the phage lambda PL promoter and other promoters known to control expression of genies in prokaryotic or eukaryotic cells or in viruses. The promoter may also be the natural promoter of the DESC1 encoding sequence. The expression vector, preferably, also contains a ribosome binding site for translation initiation and a transcription terminator. Preferably, the recombinant expression vectors also include an origin of replication and a selectable marker, such as for example, the ampicillin resistance gene of E. coli to permit selection of transformed cells, i.e. cells that are expressing the heterologous DNA sequences. The polynucleotide sequence encoding the DESC1 protein is incorporated into the vector in frame with translation initiation and termination sequences.

The polynucleotides encoding a DESC1 protein are used to express recombinant protein using conventional techniques. Such techniques are described in Sambrook, J. et al (1989) Molecular Cloning A Laboratory Manual, Cold Spring Harbor Press, Plainview, N.Y. and Ausubel, F. M. et al. (1989) Current Protocols in Molecular Biology, John wile & Sons, New York, N.Y.

Polynucleotides encoding a DESC1 protein or fragments thereof, are also useful for designing hybridization probes for isolating and identifying cDNA clones and genomic clones encoding a DESC1 protein or allelic forms thereof. Such hybridization techniques are conventional. The sequences that encode the DESC1 proteins or fragments thereof, are also useful for designing primers for polymerase chain reaction (PCR), a technique useful for obtaining large quantities of cDNA molecules that encode the DESC1 proteins.

Also encompassed by the present invention, are single stranded polynucleotides, hereinafter referred to as antisense polynucleotides, having sequences which are complementary to the DNA and RNA sequences which encode the DESC1 proteins. The term "complementary" as used herein refers to the natural binding of the polynucleotides under permissive salt and temperature conditions by base pairing.

Isolated polynucleotides encoding a DESC1 protein are also useful as chromosome markers to map related gene positions. DESC1 polynucleotide probes are preferably labeled with radioisotopes, fluorescent labels or enzymatic labels.

Polynucleotides encoding an DESC1 protein are useful to detect DESC1 gene expression in biopsied tissue samples. DESC1 polynucleotides or fragments thereof are also useful as probes or primers to identify tissues or cells in which the corresponding DESC1 gene transcript is expressed.

Proteins

The DESC1 protein possesses four regions of conserved homology with members of the serine protease gene family. The sequence identity between DESC1 protein and the serine protease, Human Airway Trypsin-like Protease (HAT) (FIG. 1B) at the amino acid level is 38% overall and 51% when the serine protease catalytic domain only is compared (DESC1 residues 191–422). This information suggests that DESC1 protein is a novel member of the serine-protease gene family.

DESC1 protein has the following conserved domains: (a) a predicted hydrophobic transmembrane domain located at about amino acids 18–37; (b) a predicted catalytic cleavage site located at about amino acids 190–191; and (c) a predicted catalytic domain located at about amino acids 191–422, containing conserved residues comprising the serine protease catalytic triad at about amino acids 231 (histidine), 276 (aspartic acid) and 372 (serine). As shown in FIG. 1, the predicted mature protein encompasses about 422 amino acids, while the predicted secreted and cleaved form of DESC1, which may be membrane-bound or soluble, encompasses about 232 amino acids (residues 191–422).

DESC1 may, similar to HAT, be a transmembrane serine protease possessing an extracellular COOH-terminal catalytic region. Accordingly, DESC1 protein may be used to cleave naturally occurring substrate proteins and by amino acid substitutions, to cleave proteins which are substrates of other serine proteases. Thus DESC1 polypeptides can be used to cleave a peptide for usage in microsequencing or for peptide mapping of proteins. DESC1 serine protease activity may be assayed utilizing standard methodologies used to demonstrate the activity of other serine proteases, as described for example by Smyth et al., J. Biol. Chem., 267: 24418–24425 and utilizing commercially available serine protease substrates including, but not limited to, Benzoyl-prolyl-phenyl-alanyl-arginine-4-nitril-anilide acetate; Tosyl-glycyl-prolyl-lysine-4-ntranilide acetate; Carbobenzoxy-valyl-glycyl-arginine-4-nitril-analide acetate and N-Methoxycarobonyl-D-norleucyl-glycl-L-arginine-4-nitranilide acetate (Boehringer Mannheim). Additionally, assay of serine protease activity of DESC1 can be utilized to identify inhibitors of DESC1 activity, by addition of known protease inhibitors to the assay, such as alpha2-macroglobulin, 2-(2-Aminoethyl)-benzyensulfonyl fluoride hydrochloride and Leupeptin (Boehringer Mannheim).

The term DESC1 protein in addition to encompassing the amino acid sequences of the reference amino acid sequences shown in FIGS. 1A and 1B, also encompasses variant DESC1 proteins whose amino acid sequence is similar to one of the reference amino acid sequences, but does not have 100% identity with the reference amino acid sequences. Such variant DESC1 protein has an altered sequence in which one or more of the amino acids is deleted or substituted, or one or more amino acids are inserted, as compared to the reference amino acid sequence. Such variant DESC1 proteins have an amino acid sequence which is at least 90% identical, preferably, at least 95% identical, more preferably at least 98% identical, most preferably at least 99% identical to the reference amino acid sequence. Sequences which are at least 90% identical have no more than 5 alterations, i.e. any combination of deletions, insertions or substitutions, per 100 amino acids of the reference amino acid sequence. Percent identity may be determined by comparing the amino acid sequence of the variant DESC1 protein with the reference sequence using MEGALIGN project in the DNA STAR program. The variant sequences and reference sequences are aligned for identity calculations using the method of the software basic local alignment search tool in the BLAST network service (the National Center for Biotechnology Information, Bethesda, Md.) which employs the method of Altschul, S. F., Gish, W., Miller, W., Myers, E. W. & Lipman, D. J. (1990) *J. Mol. Biol.* 215, 403–410. Identities are calculated, for example, by the Align, program (DNAstar, Inc.) In all cases, internal gaps and amino acid insertions in the candidate sequence as aligned are not ignored when making the identity calculation.

While variant DESC1 proteins have non-conservative amino acid substitutions, it is preferred that variant DESC1 proteins have the conservative amino acid substitutions. In conservative amino acid substitutions, the substituted amino acid has similar structural or chemical properties with the corresponding amino acid in the reference sequence. By way of example, conservative amino acid substitutions involve substitution, of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Preferably, the variant DESC1 protein is immunoreactive with antibodies that bind to the reference DESC1 protein. Guidance in determining which amino acid residues may be substituted, inserted or deleted without abolishing immunoreactivity of the variant protein with an antibody specific for the respective reference protein are found using computer programs well known in the art, for example, DNASTAR software.

The present invention also relates to fusion proteins comprising a DESC1 protein and a tag, i.e., a second protein or one or more amino acids, preferably from about 2 to 65 amino acids, more preferably from about 34 to about 62 amino acids, which are added to the amino or carboxy terminus of the DESC1 PROTEIN. Typically, such additions are made to stabilize the fusion protein or to simplify purification of an expressed recombinant form of the corresponding DESC1 protein Such tags are known in the art. Representative examples of such tags include sequences which encode a series of histidine residues, the epitope tag FLAG, the Herpes simplex glycoprotein D, beta-galactosidase, maltose binding protein, or glutathione S-transferase.

The present invention also encompasses DESC1 proteins in which one or more amino acids, preferably no more than 10 amino acids, are altered by post-translation processes or synthetic methods. Examples of such modifications include, but are not limited to, acetylation, amidation, ADP-ribosylation, covalent attachment of flavin, covalent attachment of a heme moiety, covalent attachment of a nucleotide or a lipid, cross-linking gamma-carboxylation, glycosylation, hydroxylation, iodination, methylation, myristoylation, oxidation, pegylation, proteolytic processing, phosphorylation, prenylation, racemization, sulfation, and transfer-RNA mediated additions of amino acids to proteins such as arginylation and ubiquitination.

The DESC1 protein and fragments thereof, particularly extracellular fragments thereof, are useful as immunogens to produce antibodies immunospecific for the DESC1 protein. The term "immunospecific" means the antibodies have substantially greater affinity for the DESC1 protein than for other proteins. Such antibodies include, but are not limited to, polyclonal, monoclonal, chimeric, single chain, and Fab fragments. Polyclonal antibodies are generated using conventional techniques, such as by administering the DESC1 protein or fragment thereof to a host animal. Depending on the host species, various adjuvants are preferably used to increase immunological response. Among adjuvants used in humans, BCG (bacilli Calmette-Guerin, and Corynebacterium parvum are especially preferable). Conventional techniques are also used to collect blood from the immunized animals and to isolate the serum and/or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include conventional techniques which involve competitive binding or immunoradiometric assays and typically involve the measurement of complex formation between the DESC1 protein and the antibody.

Antibodies to the DESC1 Protein

Antibodies which are specific for and bind to the DESC1 protein or the extracellular domain of the DESC1 protein, are useful research tools for identifying tissues that contain reduced levels of the DESC1 protein and also for purifying the DESC1 protein, from cell or tissue extracts, or medium of cultured cells, or partially purified preparations of intracellular and extracellular protein. Such purification is accomplished by conventional techniques such a as by affinity chromatography.

Method of Assaying for DESC1 mRNA in Tissue Samples

Expression of the DESC1 transcript in a tissue sample or cell sample is determined using conventional procedures including, but not limited to DNA-RNA hybridization or PCR amplification.

A sample of the subject's tissue is obtained from a site which is suspected as being a tumor site. Preferably, one or more tissue samples from the area adjoining or preferably distal to the putative tumor site are also obtained from the subject. More preferably, samples are also obtained from matched normal, unaffected epithelial tissue of the subject. Preferably, all tissue samples are snap-frozen in liquid nitrogen immediately following resection.

RNA is isolated from the tissue samples by conventional techniques such as a TRIzol extraction procedure see for example, Gramza et. al. "Efficient Method for Preparing Normal and Tumor Tissue for RNA Extraction" BioTechniques, volume 18, page 218 (1995) which is fully incorporated herein by reference.

The presence of DESC1 mRNA is detected by RT-PCR technology using a forward primer that anneals to a region on the antisense strand of the DESC1 gene and reverse primer which anneal to a region on the sense strand of the DESC1 gene. Preferably, the forward and reverse primers anneal to regions of the DESC1 gene which are separated by between 149 to 1471 base pairs, more preferably 300 to 400 base pairs. Preferably, the primers comprise 18–36 nucleotides, more preferably 22–31 nucleotides. Preferably, the primers have a G+C content of 40% or greater. More preferably the forward and reverse primers comprise the following sequences, respectively:

DESC1 antisense, D11, 5'-TGCATCAAGCAAACAGTT-TATTGAGATC-3' (SEQ. ID. NO. 5);

DESC1 sense, D10, 5'CCTGTTCCCTACACAAATH-CAGTAC-3' (SEQ. ID. NO. 6).

The size of the PCR product produced using such primers is 555 bp.

Optionally, a normalization standard, such as a housekeeping gene, is included in the PCR reaction. The expression of the preferred housekeeping gene is the same level in normal squamous cells and in cells derived from squamous cell carcinoma tumor tissue. For example, suitable housekeeping genes are HPRT or genes encoding actin or tubulin. Primers to the normalization standard are selected such that the length of the PCR amplification product of the normalization standard will vary from the length of the PCR amplification product of DESC1 mRNA to allow separation of the two PCR amplification products on an agarose gel.

Preferably, an internal standard comprising a double-stranded nucleic acid fragment which competes with the DESC1 gene for the primers is added to the PCR reaction mixture. Preferably, the PCR product that results from amplification of the internal standard is of a different size from that of the PCR product that results from amplification of the DESC1 mRNA to enable separation of the two products on an agarose gel.

Optimum cycle number for PCR amplification is preferably pre-determined for each primer set using a mixture of RT reactions from ten random samples selected from specimens of tumor RNA and matched normal RNA. This step is necessary to ensure that PCR amplification remains in the linear range and that production of PCR product does not plateau. Under the reaction conditions used, the quantity of PCR product is directly proportional to the amount of radioactivity incorporated into the DNA. This method allows a comparative analysis of gene expression between samples through direct comparison of radioactivity incorporated into each PCR product.

Preferably, the presence of the primer-specific PCR product is detected by separating the PCR products on an agarose gel. The presence of the primer-specific product is detected by ethidium bromide staining of the agarose gel. More preferably, the primer-specific product contains alpha-$^{32}$P-deoxynucleotide as a result of incorporating alpha-$^{32}$-p-deoxynucleotide into the PCR reaction mixture. Detection of such PCR product is accomplished by measuring the amount of radiolabeled deoxynucleotide incorporated into the PCR product by gel scanning using autoradiograms, or by liquid scintillation counting of excised portions of the gel. Band intensity of DESC1 RT-PCR product is then compared and intensity is directly proportional to the level of expression of DESC1 RNA in the original tissue sample.

Alternatively the mRNA is extracted, separated, preferably on an agarose gel, and the mRNA encoding DESC1 is detected preferably using a probe specific for such mRNA.

DESC1 RNA is expressed in normal human epithelial tissue. DESC1 RNA is also expressed in normal human epidermal keratinocytes undergoing exponential growth in tissue culture (NEHK cells; Clonetics, San Diego, Calif.). DESC1 RNA expression is reduced or absent in squamous cell carcinoma (SCC). Thus, in one embodiment, reduced DESC1 expression in neoplastic tissue of epithelial origin may be considered to be a diagnostic indicator of SCC.

Isolation and Sequence Analysis of DESC1 cDNA

Representational Difference Analysis (RDA) was performed on mRNA isolated from the normal oral buccal mucosa and from an squamous cell carcinoma-positive metastatic neck node from an individual who presented with a primary squamous cell carcinoma of the tongue which was metastatic to regional neck nodes. Representational Difference Analysis was performed with carcinoma RNA as driver in the reaction, allowing selection of genes expressed in normal tissue but not in tumor tissue. Representational Difference Analysis (RDA) was performed by utilizing PCR-Select cDNA subtraction methodologies (CLONTECH, Palo Alto, Calif.) as described in the manufacturer's protocol. 0.5% of the Representational Difference Analysis final reaction was subject to PCR amplification. The PCR amplification products thus obtained were cloned directly into mammalian expression vector pCMV-Script (Stratagene, La Jolla, Calif.).

All recombinant clones were screened for inserts by PCR analysis and positive clones subjected to sequence analysis using vector-specific T3 primers. BLASTN sequence analysis was then performed, using the GenBank sequence database. One recombinant clone designated "C35", carrying a 581 bp insert, possessed an open reading frame spanning the full length of the clone. The putative gene represented by this clone was designated Differential Expressed in Squamous Cell Carcinoma Gene 1 (DESC1). The C35 clone was devoid of consensus polyadenylation signals. In order to obtain the 3' end of the gene, 3'RACE analysis was performed on the remaining normal tissue mRNA used previously for RDA analysis. Sequence analysis of 3'RACE products allowed identification of two consensus polyadenylation signal sequences separated by 633 bp (FIG. 1A). In order to obtain additional 5' sequence, 5'RACE was also performed.

A full-length DESC1 cDNA clone (pDESC1) was constructed following analysis of DESC1 sequence information obtained from overlapping pCMV-Script, 5' and 3' RACE clones. pDESC1 was generated by RT-PCR amplification of normal skin RNA (Invitrogen, Carlsbad, Calif.) utilizing DESC1 primers D11 and D12. primers D11 and D12 have the following sequence:

D11, 5'-TGCATCAAGCAAACAGTTTATTGAGATC-3' (SEQ. ID. NO. 5);

D12, 5'TGACTTGGATGTAGACCTCGACCTTCAC-3' (SEQ. ID. NO. 7).

The PCR product was then cloned into TOPO TA cloning vector pCDNA3.1/V5/His-Topo (Invitrogen, Carlsbad, Calif.). The sequence of pDESC1 was determined by cycle sequencing using a Thermo Sequenase system (Amersham, Cleveland, Ohio), followed by electrophoresis using the CastAway sequencing system (Stratagene, La Jolla, Calif.) according to the manufacturer's instructions.

The full-length nucleotide sequence (SEQ ID NO:1) of one cDNA encoding DESC 1 protein is shown in FIG. 1A.

An alternate full-length nucleotide sequence, SEQ.ID.NO. 3 is shown in FIG. 1B. The cDNA comprises a contiguous sequence of 1461 nucleotides which encodes a predicted open reading frame of 422 or 423 amino acid residues (SEQ ID NO:2). The open reading frame begins at an N-terminal methionine located at nucleotide position 53 or 56, and ends at a stop codon at nucleotide position 1322. The predicted molecular weight of the DESC1 protein is about 44 kDa.

Tissue Expression of DESC1

Figure 5A:
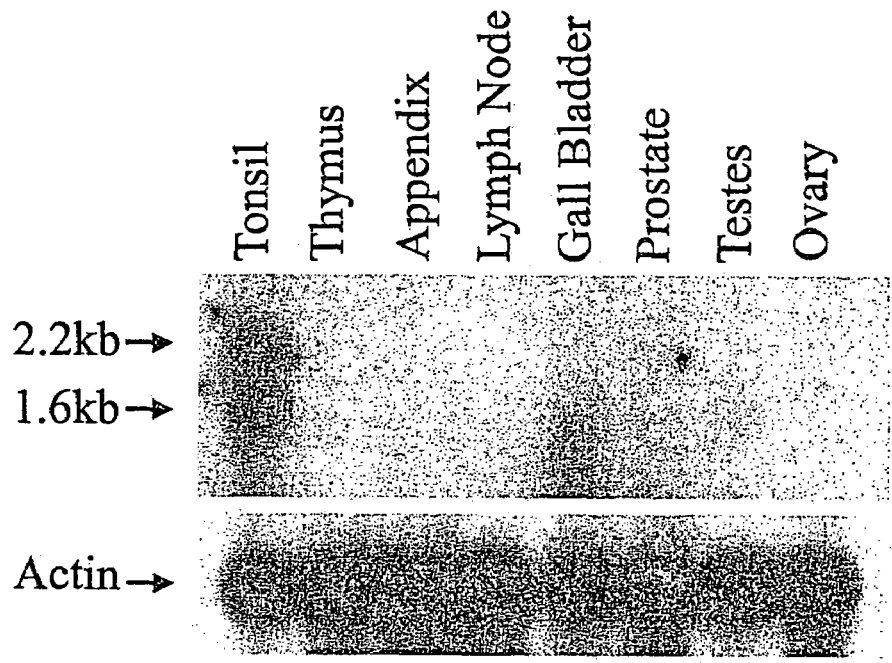
FIG. 5. Expression of DESC1 in multiple human tissues. Northern analysis using A total RNA (Human Normal Tissue Blot III) and B, polyadenylated RNA (Human Multiple Tissue Northern Blot II)
Figure 5B:
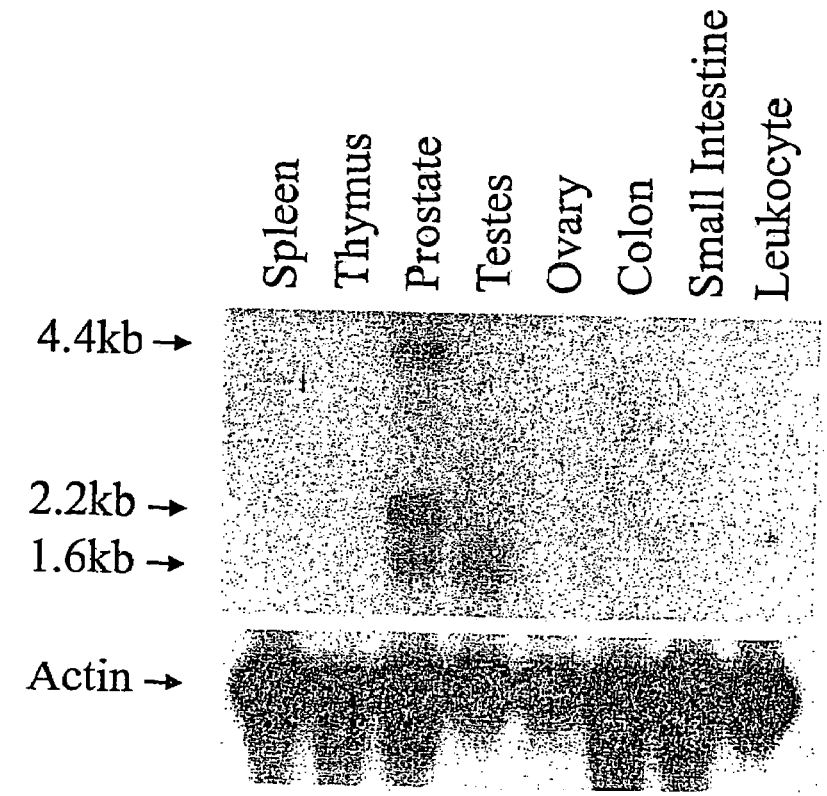
Figure 6:
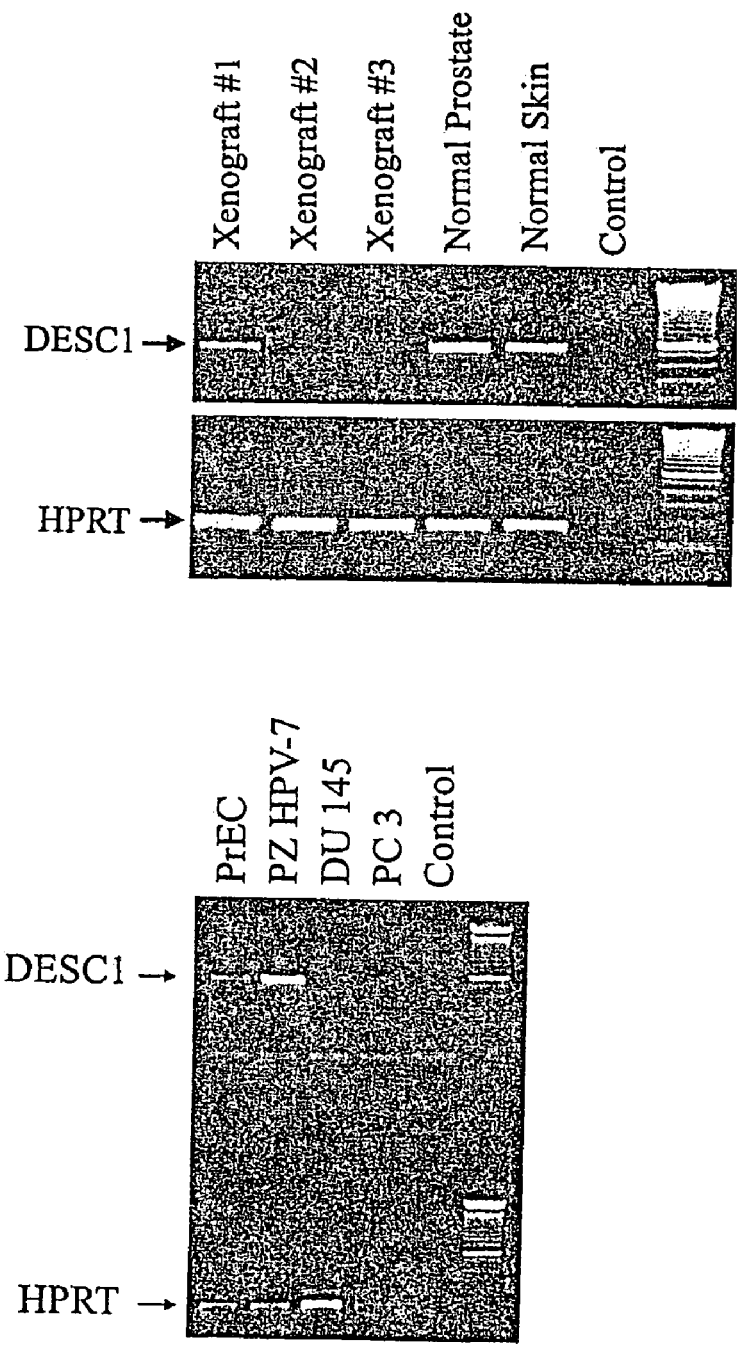
FIG. 6. Expression of DESC1 in prostate cancer specimens and clel lines. RT-PCR analysis of (A) prostate cancer xenografts shown in mice and (B) human prostate cell lines FIG. 7. Expression of DESC1 in transfected human embryonal kidney epithelial cells. Western Analysis of lysates from cells FIG. 8. Protease Activity of recombinant DESC1 protein purified from transfected COS cells.
Figure 7:
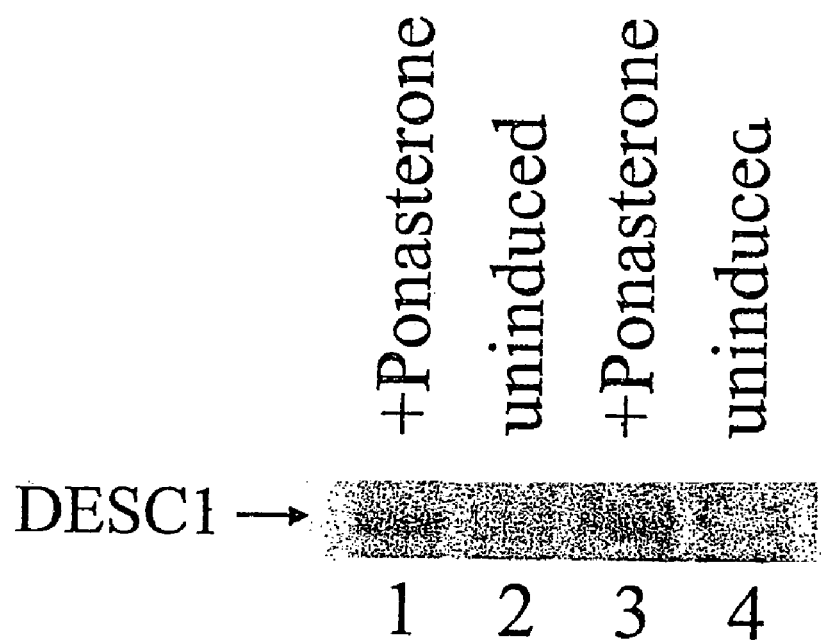
Figure 8:
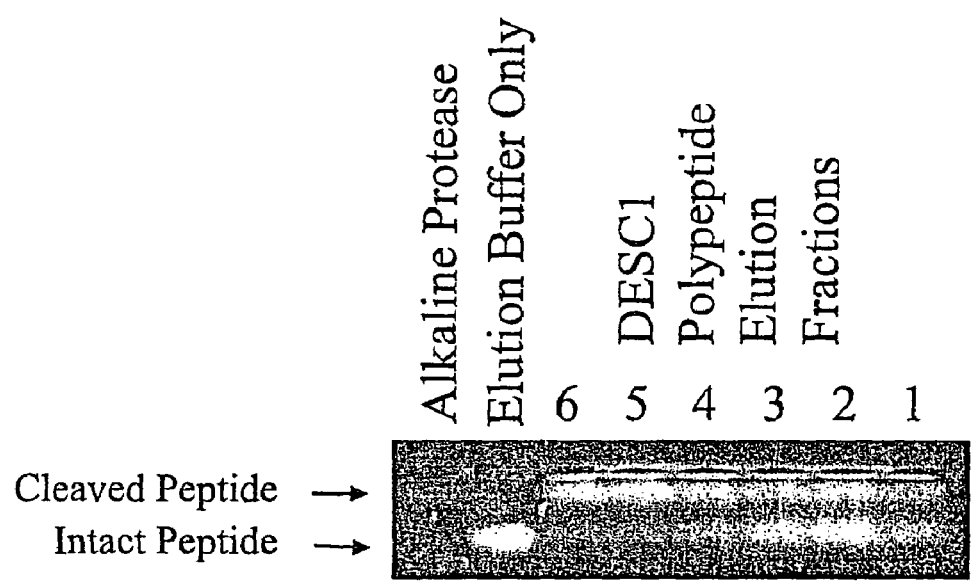

In order to characterize the tissue-specific expression pattern of DESC1, Northern analysis was performed on total RNA from multiple human tissue samples and cell lines. The results are shown in FIG. 5 and demonstrate a high degree of tissue specificity of DESC1 expression. Under these conditions two predominant transcripts of 2.2 kb and 1.6 kb in size were detected in tonsil tissue. Under these conditions no significant level of DESC1 expression was detected in any other tissue examined, that is thymus, appendix, lymph node, gall bladder, ovary, spleen, colon small intestine, leukocyte, heart, brain, placenta, lung, liver, skeletal muscle, kidney prostate and testes. However, when Northern analysis was performed with a higher degree of sensitivity, utilizing polyadenylated RNA rather than total RNA, DESC1 expression was detected in prostate and testes. A single 1.6 kb transcript is seen in testes. The three transcripts detected in prostate include a 1.6 kb transcript a 2.2 kb transcript and an additional transcript of approximately 4.4 kb, which is observed exclusively in prostate tissue. In addition, expression of DESC1 was detected at a minimal level in pancreas. No expression of DESC1 was detected in thymus, appendix, lymph node, gall bladder, ovary, spleen, colon small intestine, leukocyte, heart, brain, placenta, lung, liver, skeletal muscle, and kidney. Thus, the DESC1 gene is strongly tissue-specific in its pattern of expression.

Figure 4:
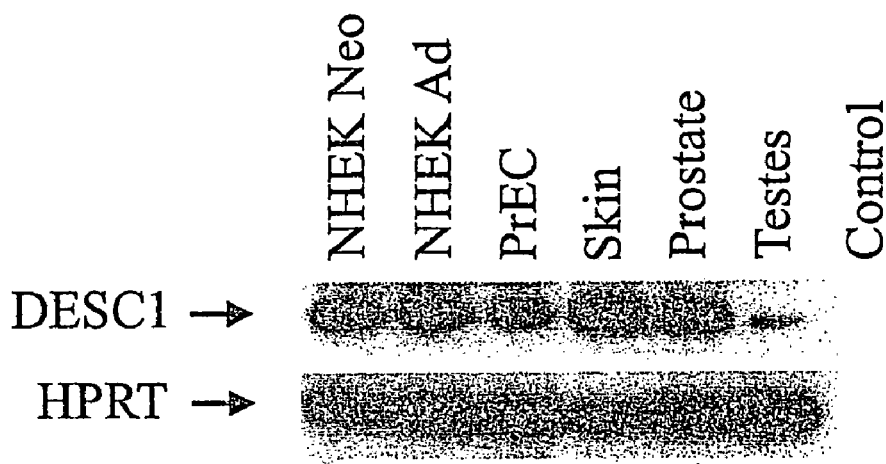
FIG. 4. Expression of DESC1 in epithelial cell lines and human tissues. RT-PCR analysis using total RNA derived from epithelial cell lines and human tissues. Primers utilized, D10 and D11.

To determine whether DESC1 expression was epithelial-specific, the levels of DESC1 transcripts in epithelial cell lines and tissue were determined using RT-PCR analysis. The results, shown in FIG. 4 established that DESC1 is expressed in neonatal (NHEKNeo) adult (NHEKAd) and prostate (PrEC) epithelial cells, confirming that the expression of the DESC1 gene is epithelial specific. FIG. 4 also shows DESC1 expression in human skin and confirms expression in prostate and testes.

The RT-PCR analysis utilized primers D10 and D11, specific to the 3' end of DESC1, and produced a product that does not encompass the internal polyadenylation consensus site. This analysis allows detection of DESC1 expression in testes. Since testes exhibits only the smaller 1.6 kb transcript, the data is consistent with identification of the 1.6 kb RNA as the transcript which encodes the DESC1 polypeptide. A second 3' RACE product isolated demonstrates processing of a DESC1 RNA at the internal polyadenylation site (nucleotides 802–807). This transcript terminates at nucleotide 823 and demonstrates that the internal site is functional.

Chromosomal Mapping Using a DESC1 Probe.

Chromosomal mapping of DESC1 gene was performed using a Human/Rodent Somatic Cell Hybrid Panel from Oncor, Gaithersburg, Md., with hybridization conditions for DESC1 probe as described above. The DESC1 probe hybridized to only the lane containing human chromosome 4. Chromosomal mapping of DESC1 was additionally performed using the Genebridge 4 Radiation Hybrid Panel (Research Genetics Inc., Huntsville, Ala.) according to the manufacturer's instructions by PCR amplification using primers D11 and D18, with normal human placental DdnA (Sigma, St. Louis, Mo.) as template. D18 primer has the following sequence, 5'-GGAATAGTGAGCTCGG-GAGATG-3' (SEQ. ID. NO. 8).

The chromosomal location of DESC1 was then determined by accessing Whitehead Institute/MIT Center for Genome Research radiation hybrid map of the human genome. DESC1 is located on the long, arm of chromosome 4, positioned 20.21cR from marker WI-5548, and between markers D4S1619 and WI-7844. D4S1619 and WI-7844 have been mapped by FISH analysis to 4q12 and 4q13. Thus DESC1 is at 4q12–4q13 within a region about 10 Mb in size The following examples, which describe in greater detail the procedures for determining DESC1 gene expression levels in tissue samples, are intended to illustrate but not limit the procedures.

EXAMPLE 1

Ten squamous cell carcinoma specimens, and matched normal tissue, selected from diverse sites in the head and neck region were obtained. All normal tissue specimens were harvested from clinically appearing normal tissue located at least 3 cm. from the tumor margin. RNA was extracted from the samples and subjected to RT-PCR analysis. of expression of DESC1 was conducted in the samples.

1.0 µg of total RNA was used for first strand cDNA synthesis in a total volume of 25 µl and reactions otherwise performed according to manufacturer's instructions (ProSTAR, Stratagene, La Jolla, Calif.). PCR amplification was performed in the presence of 2 units of Taq 2000 DNA polymerase (Stratagene, La Jolla, Calif.), with reaction conditions: 10 mM Tris-HCl (pH 8.8), 50 mM KCl, 1.5 mM MgCl$_2$, 0.01% gelatin, 400 nM each primer, 200 µM dNTPs, and where appropriate, 0.25 µl [$\alpha^{32}$P]dCTP (3000Ci/mmol) in a final volume of 25 µl. Separate reactions were performed for each primer pair with reaction conditions; 96° C. 3 min followed by 94° C. 30s, 55° C. 30's, 72° C. 1 min for 31 cycles (HPRT) or 33 cycles (DESC1) and a final 5 min extension at 72° C. PCR amplification of full-length DESC1 was performed utilizing the above cycling conditions, with an additional 1 min extension time for each cycle at 72° C., and using the Advantage HF PCR kit (CLONTECH Laboratories Ind, Palo Alto, Calif.). PCR samples were then run through 22% agarose gels and presence of amplified product and correct product size verified by ethidium bromide fluorescence in the presence of 100 bp size markers (Gibco BRL, Gaithersburg, Md.). PCR products generated were then electroblotted using a Bio-Rad Semi-Dri Electroblotter SD and transferred at 12V/110 mA for 10 min. The membrane was removed and exposed to BioMax film (Eastman Kodak, Rochester, N.Y.). Primers utilized in PCR reactions comprise: hypoxanthine phosphoribosyl transferase (HPRT) primers HPt1, 5'-GTAATGACCAGTCAACA-3' (SEQ. ID. NO. 11) and HPRT2, 5'-CCAGCAAGCTTGCGACCT-TGACCA-3' (SEQ. ID. NO. 12) and DESC1 primers

D3, 5'-TCACTGTTCATTATGTGAGATATAATCA-3' (SEQ. ID. NO. 9);

D4, 5'-CACCATTGATTCAAGTCTCTGGCTCAT-3' (SEQ. ID. NO. 10);

D10, 5'-CCTGTTCCCTACACAAATGCAGTAC-3' (SEQ. ID. NO. 6);

D11, 5'-TGCATCAAGCAAACAGTTTATTGAGATC-3' (SEQ. ID. NO. 5);

D12, 5'-TGACTTGGATGTAGACCTCGACCTTCAC-3' (SEQ. ID. NO. 7) and

D18, 5'-GGAATAGTGAGCTCGGGAGATG-3' (SEQ. ID. NO. 8).

PCR amplification of the HPRT gene was performed as a control to demonstrate equal loading and to determine integrity of RNA. Primers sets were designed by computer analysis (Oligo 4.0; NBI, Hamel, MN) of available DNA sequences for each gene and, with the exception of set D11, D18, are intron-spanning precluding PCR amplification of any residual DNA present in RNA samples. Optimum cycle number for PCR amplification was pre-determined for each primer set using a mixture of RT reactions from ten random tumor samples. This step is necessary to ensure that PCR amplification remains in the linear range and that production of PCR product does not plateau. Under reaction conditions used, quantity of PCR product is therefore directly proportional to the amount of radioactivity incorporated into the DNA.

Figure 3A:
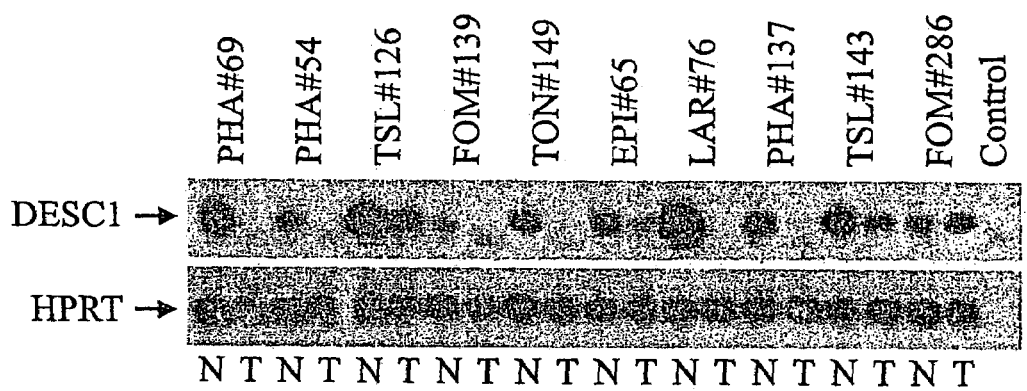
FIG. 3. Expression of DESC1 in squamous cell carcinoma of the head and neck (SSCHN) and matched normal tissues. A, RT-PCR analysis of DESC1 expression in SCCHN and matched normal tissue. Primers utilized: D3, D4. Size of RT-PCR product 149 bp. Low molecular weight band seen in negative control lane and some sample lanes represents unincorporated [$\alpha^{32}$P]dCTP. B, Northern analysis of DESC1 expression in SCCHN, matched normal tissue and metastatic neck node. PHA, pharynx; TSL, tonsil; FOM, floor of mouth; TON, tongue; EPI, epiglotis; LAR, larynx; R T, retromolar trigone; T B, tongue base.

The results, shown in FIG. 3A, showed lower levels of expression of DESC1 in 9 of the 10 primary carcinomas relative to the high level of expression in matched normal tissue. It has been discovered that in non cancerous epithelial tissue, DESC1 is expressed at a high level, yet in squamous cell carcinoma, DESC1 is not expressed or only expressed at a very low level, i.e., at levels less than 10% of the levels found in matched normal tissue

EXAMPLE 2

Six specimens of squamous cell carcinoma of the head and neck, matched normal tissue and metastatic regional neck nodes were obtained. The mRNA extraction was conducted as in Example 1. A northern blot containing squamous cell carcinoma specimens was generated by electrophoresis of 10 µg total RNA on a 1% glyoxal agarose gel according to manufacturer's instructions (Northern Max-Gly, Ambion, Austin, Tex.). Blots were hybridized with [$\alpha^{32}$P]dCTP-labeled DESC1 cDNA probe spanning 581 nucleotides of the DESC1 coding sequence (nucleotides 165–746), or control β-actin cDNA (CLONTECH Laboratories Inc., Palo Alto, Calif.), according to manufacturer's protocol. Blots were then washed in 0.5×SSC, 0.1% SDS for 30 min. at room temperature, followed by 0.1×SSC, 0.1% SDS for 1 hr. at 50° C. with two changes of solution. The blots were then exposed to BioMax film.

Figure 3B:
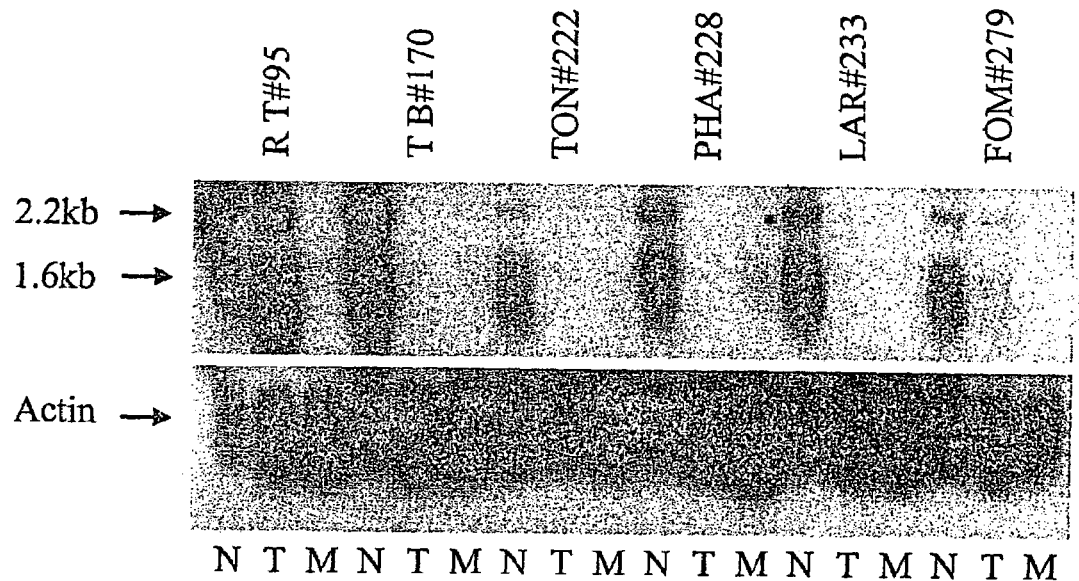

As shown in FIG. 3B, expression of DESC1 was lower in squamous cell carcinoma specimens relative to matched normal specimens. Additionally, DESC1 expression was not detected in any metastatic nodal tissue samples, with the exception of minimal expression in a pharyngeal carcinoma metastatic to regional neck nodes.

EXAMPLE 3

Specimens for analysis comprising primary carcinoma, metastatic node and matched normal tissue were obtained from an individual who presented with a primary squamous cell carcinoma of the tongue which was metastatic to regional neck nodes. The mRNA extraction, amplification and analysis for expression of DESC1 was conducted as in Example 1. As shown in FIG. 2, DESC1 was expressed at a high level in normal tissue sample but, in contrast, was expressed at a very low level in the primary tongue carcinoma and absent from the metastatic nodal tissue derived from the same individual.

Notably, little to no DESC1 PCR transcripts were detected in the tumor samples of Examples 1–3. These results show that the present method is useful for determining the levels of DESC1 mRNA in tumor tissue from individuals with squamous cell carcinoma and for distinguishing squamous cell carcinoma tissue from healthy tissue. Such method is also useful to determine whether expression is absent, present, or altered. Thus, the present method is also useful for research purposes to determine whether therapeutic agents modulate expression of the DESC-1 gene.

EXAMPLE 4

The DESC1 gene has been cloned into mammalian expression vector pcDNA3.1/V5/His-TOPO, in both the sense and anti-sense direction. These constructs and the empty vector alone were transfected into NIH3T3 cells and stable colonies were obtained via use of the neomycin resistance gene present on the sample plasmid. Colonies obtained were counted. Total colony count for two flasks transfected with DESC1 sense construct is 128. Total colony count for two flasks transfected with anti-sense DESC1 construct is 301. Total colony count for two flasks transfected with empty vector alone is 245. Additionally, A colonies from DESC1 sense construct were smaller, suggesting that the growth rate of the colonies was slower. Thus, the present invention also relates to a method altering replication or growth of host cells by introducing a polynucleotide which encodes the DESC1 into such cells and then expressing the polynucleotide.

EXAMPLE 5

Expression of DESC1 in Prostate Cancer Specimens and Cell Lines

Expression of DESC1 was assayed in specimens of human prostate cancer and prostate cancer cell lines. RT-PCR analysis of DESC1 expression was performed using PCR primers D10 and D11 previously used to assay for expression of DESC1 in squamous cell carcinomas of the head and neck. The results show lack of DESC1 expression in ⅔ human prostate cancer xenografts grown in mice. Expression of DESC1 is also undetectable in human prostate cancer cell lines DU145 and PC3. However, expression of DESC1 can be detected in normal human prostate tissue, normal human prostate epithelial cells (PrEC cells, Clonetics) and in normal prostate cells immortalized with HPV (PZ HPV-7).

EXAMPLE 6

Western Analysis of DESC1 Expression in Transfected Human Embryonal Kidney Epithelial Cells The DESC1 cDNA was cloned into ecdysone-inducible mammalian expression vector pIND Topo TA to produce recombinant clone pDESC1/IND C4. In this clones the DESC1 polypeptide is expressed as a fusion protein with a carboxy-terminal tag containing the V5 epitope from the paramyxovirus SV5. When expressed in mammalian cells, DESC1 can then be detected by Western analysis utilizing an antibody to the V5 epitope. PDESC1/InD C4 was transfected into human embroyonal kidney epithelial calls (293 cells) previously engineered to express the insect ecdysone receptor. Transfection of pDESC1/InD C4 was performed using Effectene (Qiagen) transfection reagent. Expression of DESC1 from this recombinant clone was accomplished by addition of Ponasterone (a synethetic analog of ecdysone) which allows binding of the ecdysone receptor to its response element ill the promoter controlling DESC1 expression according to the manufacturer's instructions (Invitrogen). 72 hours post transfection, cell lysates were made from 293 cells both treated and untreated with Ponasterone. Lysates were then run on NuPAGE acrylamide gels (Novex) and Western analysis performed utilizing a chemiluminescent Western blotting immunodetection system (Novex). The results are shown below and demonstrate presence of a polypeptide approximately 52 kd in lanes 1 and 3 (ponasterone induced) but not in lanes 2 and 4 (ponasterone negative). The molecular weight of 52 kd is consistent with the predicted size of the fusion polypeptide produced by DESC1 (47 kd) and the fused V4/HIS Tag epitopes (5 kd).

EXAMPLE 7

Expression of DESC1 in COS Cells, Purification of Recombinant Protein and Assay for Protease Activity DESC1 full length cDNa was cloned into mammalian expression vector pcDNA4/HisMax (Invitrogen). In this recombinant construct, the DESC1 polypeptide is expressed as a fusion protein with an amino-terminal His tag. DNA was transfected into COS cells utilizing Superfect transfection reagent. 72 hours after transfection, cells were lysed and recombinant DESC1 polypeptide purified utilizing the Xpress protein purification system (Invitrogen) according to the manufacturer's instructions. Purification was accomplished via binding of the His tag to ProBond resin and subsequent elution of the recombinant polypeptide. Protease activity was then tested by incubation of DESC1 recombinant polypeptide in a PepTag Protease Assay. In this assay, presence of protease activity is demonstrated by proteolysis of small dye-linked peptides. Digestion of the peptides alters the size and charge, and these changes can be detected by agarose gel electrophoresis. DESC1 polypeptide was incubated with PepTag peptide C1, with sequence: Dye-Pro-Leu-Ser-Arg-Thr-Leu-Ser-Val-Ala-Ala-Lys (SEQ. ID. NO. 13). Proteolytic cleavage between the C-terminal lysine and the internal arginine yields fragments with a neutral charge which remain in the well on electrophoresis. Intact peptide has a net positive charge and migrates towards the negative electrode. Protease activity was measured according to the manufacturer's protocol (Promega). The results are shown below and demonstrate proteolytic cleavage of C1 peptide by fractions containing DESC1 polypeptide eluted from the ProBond resin. Results show increasing activity within fractions 1–6, while peptide incubated with elution buffer alone (lane 7) shows no protease activity (peptide intact). Positive control alkaline protease demonstrates protease activity (lane 8) similar to that of DESC1 fractions.

What is claimed is:

1. A method for detecting the presence of at least one of squamous cell carcinoma and prostate cancer in a subject comprising: providing from the subject a tissue sample that is suspected of being cancerous, wherein the tissue sample is obtained from one or more of the head, neck, and prostate of the subject; providing at least one nucleic acid probe or primer that is capable of hybridizing under stringent conditions with a nucleic acid having the sequence of either SEQ ID NO:1 or SEQ ID NO:3; and assaying the sample with at least one nucleic acid probe or primer to detect in the sample ribonucleic acid the is capable of hybridizing under stringent conditions with the at least one probe or primer; wherein reduced level of detected ribonucleic acid, as compared to normal tissue sample taken from the same tissue of the same subject, is indicative of the presence of at least one squamous cell carcinoma and prostate cancer.

2. The method according to claim 1, wherein the tissue sample is obtained from one or more of the head and neck of the subject.

3. The method according to claim 1, wherein the tissue sample is obtained from the prostate of the subject.

4. The method according to claim 1, wherein the at least one probe or primer is capable of hybridizing under stringent conditions with a nucleic acid having the sequence of either nucleotides 626–1321 of SEQ ID NO: 1 or nucleotides 626–1321 of SEQ ID NO: 3.

5. The method according to claim 1, wherein the at least one nucleic acid probe or primer is chosen from SEQ ID NO: 5, SEQ ID NO: 6, SEQ ID NO: 7, SEQ ID NO: 8, SEQ ID NO: 9, and SEQ ID NO: 10.

* * * * *

SEQUENCE LISTING

<160> NUMBER OF SEQ ID NOS: 13

<210> SEQ ID NO 1
<211> LENGTH: 1471
<212> TYPE: DNA
<213> ORGANISM: Homo sapiens
<220> FEATURE:
<221> NAME/KEY: CDS
<222> LOCATION: (56)..(1324)
<223> OTHER INFORMATION:

<400> SEQUENCE: 1

```
tgacttggat gtagacctcg accttcacag gactcttcat tgctggttgg caatg atg                58
                                                             Met
                                                              1 tat cgg cca gat gtg gtg agg gct agg aaa aga gtt tgt tgg gaa ccc             106
Tyr Arg Pro Asp Val Val Arg Ala Arg Lys Arg Val Cys Trp Glu Pro
         5                  10                  15 tgg gtt atc ggc ctc gtc atc ttc ata tcc ctg att gtc ctg gca gtg             154
Trp Val Ile Gly Leu Val Ile Phe Ile Ser Leu Ile Val Leu Ala Val
     20                  25                  30 tgc att gga ctc act gtt cat tat gtg aga tat aat caa aag aag acc             202
Cys Ile Gly Leu Thr Val His Tyr Val Arg Tyr Asn Gln Lys Lys Thr
 35                  40                  45 tac aat tac tat agc aca ttg tca ttt aca act gac aaa cta tat gct             250
Tyr Asn Tyr Tyr Ser Thr Leu Ser Phe Thr Thr Asp Lys Leu Tyr Ala
 50                  55                  60                  65 gag ttt ggc aga gag gct tct aac aat ttt aca gaa atg agc cag aga             298
Glu Phe Gly Arg Glu Ala Ser Asn Asn Phe Thr Glu Met Ser Gln Arg
                 70                  75                  80 ctt gaa tca atg gtg aaa aat gca ttt tat aaa tct cca tta agg gaa             346
Leu Glu Ser Met Val Lys Asn Ala Phe Tyr Lys Ser Pro Leu Arg Glu
             85                  90                  95 gaa ttt gtc aag tct cag gtt atc aag ttc agt caa cag aag cat gga             394
Glu Phe Val Lys Ser Gln Val Ile Lys Phe Ser Gln Gln Lys His Gly
         100                 105                 110 gtg ttg gct cat atg ctg ttg att tgt aga ttt cac tct act gag gat             442
Val Leu Ala His Met Leu Leu Ile Cys Arg Phe His Ser Thr Glu Asp
     115                 120                 125 cct gaa act gta gat aaa att gtt caa ctt gtt tta cat gaa aag ctg             490
Pro Glu Thr Val Asp Lys Ile Val Gln Leu Val Leu His Glu Lys Leu
 130                 135                 140                 145 caa gat gct gta gga ccc cct aaa gta gat cct cac tca gtt aaa att             538
Gln Asp Ala Val Gly Pro Pro Lys Val Asp Pro His Ser Val Lys Ile
                 150                 155                 160 aaa aaa atc aac aag aca gaa aca gac agc tat cta aac cat tgc tgc             586
Lys Lys Ile Asn Lys Thr Glu Thr Asp Ser Tyr Leu Asn His Cys Cys
             165                 170                 175 gga aca cga aga agt aaa act cta ggt cag agt ctc agg atc gtt ggt             634
Gly Thr Arg Arg Ser Lys Thr Leu Gly Gln Ser Leu Arg Ile Val Gly
         180                 185                 190 ggg aca gaa gta gaa gag ggt gaa tgg ccc tgg cag gct agc ctg cag             682
Gly Thr Glu Val Glu Glu Gly Glu Trp Pro Trp Gln Ala Ser Leu Gln
     195                 200                 205 tgg gat ggg agt cat cgc tgt gga gca acc tta att aat gcc aca tgg             730
Trp Asp Gly Ser His Arg Cys Gly Ala Thr Leu Ile Asn Ala Thr Trp
 210                 215                 220                 225 ctt gtg agt gct gct cac tgt ttt aca aca tat aag aac cct gcc aga             778
Leu Val Ser Ala Ala His Cys Phe Thr Thr Tyr Lys Asn Pro Ala Arg
                 230                 235                 240
```

```
tgg act gct tcc ttt gga gta aca ata aaa cct tcg aaa atg aaa cgg      826
Trp Thr Ala Ser Phe Gly Val Thr Ile Lys Pro Ser Lys Met Lys Arg
        245                 250                 255 ggt ctc cgg aga ata att gtc cat gaa aaa tac aaa cac cca tca cat      874
Gly Leu Arg Arg Ile Ile Val His Glu Lys Tyr Lys His Pro Ser His
        260                 265                 270 gac tat gat att tct ctt gca gag ctt tct agc cct gtt ccc tac aca      922
Asp Tyr Asp Ile Ser Leu Ala Glu Leu Ser Ser Pro Val Pro Tyr Thr
275                 280                 285 aat gca gta cat aga gtt tgt ctc cct gat gca tcc tat gag ttt caa      970
Asn Ala Val His Arg Val Cys Leu Pro Asp Ala Ser Tyr Glu Phe Gln
290                 295                 300                 305 cca ggt gat gtg atg ttt gtg aca gga ttt gga gca ctg aaa aat gat     1018
Pro Gly Asp Val Met Phe Val Thr Gly Phe Gly Ala Leu Lys Asn Asp
                310                 315                 320 ggt tac agt caa aat cat ctt cga caa gca cag gtg act ctc ata gac     1066
Gly Tyr Ser Gln Asn His Leu Arg Gln Ala Gln Val Thr Leu Ile Asp
                325                 330                 335 gct aca act tgc aat gaa cct caa gct tac aat gac gcc ata act cct     1114
Ala Thr Thr Cys Asn Glu Pro Gln Ala Tyr Asn Asp Ala Ile Thr Pro
                340                 345                 350 aga atg tta tgt gct ggc tcc tta gaa gga aaa aca gat gca tgc cag     1162
Arg Met Leu Cys Ala Gly Ser Leu Glu Gly Lys Thr Asp Ala Cys Gln
        355                 360                 365 ggt gac tct gga gga cca ctg gtt agt tca gat gct aga gat atc tgg     1210
Gly Asp Ser Gly Gly Pro Leu Val Ser Ser Asp Ala Arg Asp Ile Trp
370                 375                 380                 385 tac ctt gct gga ata gtg agc tgg gga gat gaa tgt gcg aaa ccc aac     1258
Tyr Leu Ala Gly Ile Val Ser Trp Gly Asp Glu Cys Ala Lys Pro Asn
                390                 395                 400 aag cct ggt gtt tat act aga gtt acg gcc ttg cgg gac tgg att act     1306
Lys Pro Gly Val Tyr Thr Arg Val Thr Ala Leu Arg Asp Trp Ile Thr
                405                 410                 415 tca aaa act ggt atc taa gagagaaaag cctcatggaa cagataacat            1354
Ser Lys Thr Gly Ile
            420 ttttttttgt ttttgggtg tggaggccat ttttagagat acagaattgg agaagacttg    1414 caaaacagct agatttgact gatctcaata aactgtttgc ttgatgcaaa aaaaaaa      1471

<210> SEQ ID NO 2
<211> LENGTH: 422
<212> TYPE: PRT
<213> ORGANISM: Homo sapiens

<400> SEQUENCE: 2

Met Tyr Arg Pro Asp Val Val Arg Ala Arg Lys Arg Val Cys Trp Glu
1               5                   10                  15

Pro Trp Val Ile Gly Leu Val Ile Phe Ile Ser Leu Ile Val Leu Ala
                20                  25                  30

Val Cys Ile Gly Leu Thr Val His Tyr Val Arg Tyr Asn Gln Lys Lys
            35                  40                  45

Thr Tyr Asn Tyr Tyr Ser Thr Leu Ser Phe Thr Thr Asp Lys Leu Tyr
        50                  55                  60

Ala Glu Phe Gly Arg Glu Ala Ser Asn Asn Phe Thr Glu Met Ser Gln
65                  70                  75                  80

Arg Leu Glu Ser Met Val Lys Asn Ala Phe Tyr Lys Ser Pro Leu Arg
                85                  90                  95
```

-continued

```
Glu Phe Val Lys Ser Gln Val Ile Lys Phe Ser Gln Gln Lys His
         100                 105                 110
Gly Val Leu Ala His Met Leu Leu Ile Cys Arg Phe His Ser Thr Glu
         115                 120                 125
Asp Pro Glu Thr Val Asp Lys Ile Val Gln Leu Val Leu His Glu Lys
         130                 135                 140
Leu Gln Asp Ala Val Gly Pro Pro Lys Val Asp Pro His Ser Val Lys
145                 150                 155                 160
Ile Lys Lys Ile Asn Lys Thr Glu Thr Asp Ser Tyr Leu Asn His Cys
                165                 170                 175
Cys Gly Thr Arg Arg Ser Lys Thr Leu Gly Gln Ser Leu Arg Ile Val
                180                 185                 190
Gly Gly Thr Glu Val Glu Glu Gly Trp Pro Trp Gln Ala Ser Leu
         195                 200                 205
Gln Trp Asp Gly Ser His Arg Cys Gly Ala Thr Leu Ile Asn Ala Thr
         210                 215                 220
Trp Leu Val Ser Ala Ala His Cys Phe Thr Thr Tyr Lys Asn Pro Ala
225                 230                 235                 240
Arg Trp Thr Ala Ser Phe Gly Val Thr Ile Lys Pro Ser Lys Met Lys
                245                 250                 255
Arg Gly Leu Arg Arg Ile Ile Val His Glu Lys Tyr Lys His Pro Ser
                260                 265                 270
His Asp Tyr Asp Ile Ser Leu Ala Glu Leu Ser Ser Pro Val Pro Tyr
         275                 280                 285
Thr Asn Ala Val His Arg Val Cys Leu Pro Asp Ala Ser Tyr Glu Phe
         290                 295                 300
Gln Pro Gly Asp Val Met Phe Val Thr Gly Phe Gly Ala Leu Lys Asn
305                 310                 315                 320
Asp Gly Tyr Ser Gln Asn His Leu Arg Gln Ala Gln Val Thr Leu Ile
                325                 330                 335
Asp Ala Thr Thr Cys Asn Glu Pro Gln Ala Tyr Asn Asp Ala Ile Thr
                340                 345                 350
Pro Arg Met Leu Cys Ala Gly Ser Leu Glu Gly Lys Thr Asp Ala Cys
         355                 360                 365
Gln Gly Asp Ser Gly Gly Pro Leu Val Ser Ser Asp Ala Arg Asp Ile
         370                 375                 380
Trp Tyr Leu Ala Gly Ile Val Ser Trp Gly Asp Glu Cys Ala Lys Pro
385                 390                 395                 400
Asn Lys Pro Gly Val Tyr Thr Arg Val Thr Ala Leu Arg Asp Trp Ile
                405                 410                 415
Thr Ser Lys Thr Gly Ile
                420
```

<210> SEQ ID NO 3
<211> LENGTH: 1471
<212> TYPE: DNA
<213> ORGANISM: Homo sapiens
<220> FEATURE:
<221> NAME/KEY: CDS
<222> LOCATION: (56)..(1324)
<223> OTHER INFORMATION:

<400> SEQUENCE: 3

```
tgacttggat gtagacctcg accttcacag gactcttcat tgctggttgg caatg atg    58
                                                            Met
                                                            1
```

| | |
|---|---|
| tat cgg cca gat gtg gtg agg gct agg aaa aga gtt tgt tgg gaa ccc<br>Tyr Arg Pro Asp Val Val Arg Ala Arg Lys Arg Val Cys Trp Glu Pro<br>          5                      10                15 | 106 |
| tgg gtt atc ggc ctc gtc atg ttc ata tcc ctg att gtc ctg gca gtg<br>Trp Val Ile Gly Leu Val Met Phe Ile Ser Leu Ile Val Leu Ala Val<br>         20                 25                 30 | 154 |
| tgc att gga gtc act gtt cat tat gtg aga tat aat caa aag aag acc<br>Cys Ile Gly Val Thr Val His Tyr Val Arg Tyr Asn Gln Lys Lys Thr<br>35                   40                 45 | 202 |
| tac aat tac tat agc aca ttg tca ttt aca act gac aaa cta tat gct<br>Tyr Asn Tyr Tyr Ser Thr Leu Ser Phe Thr Thr Asp Lys Leu Tyr Ala<br>50                   55                 60                 65 | 250 |
| gag ttt ggc aga gag gct tct aac aat ttt aca gaa atg agc cag aga<br>Glu Phe Gly Arg Glu Ala Ser Asn Asn Phe Thr Glu Met Ser Gln Arg<br>               70                    75                80 | 298 |
| ctt gaa tca atg gtg aaa aat gca ttt tat aaa tct cca tta agg gaa<br>Leu Glu Ser Met Val Lys Asn Ala Phe Tyr Lys Ser Pro Leu Arg Glu<br>                   85                90                95 | 346 |
| gaa ttt gtc aag tct cag gtt atc aag ttc agt caa cag aag cat gga<br>Glu Phe Val Lys Ser Gln Val Ile Lys Phe Ser Gln Gln Lys His Gly<br>         100                   105              110 | 394 |
| gtg ttg gct cat atg ctg ttg att tgt aga ttt cac tct act gag gat<br>Val Leu Ala His Met Leu Leu Ile Cys Arg Phe His Ser Thr Glu Asp<br>115                 120                 125 | 442 |
| cct gaa act gta gat aaa att gtt caa ctt gtt tta cat gaa aag ctg<br>Pro Glu Thr Val Asp Lys Ile Val Gln Leu Val Leu His Glu Lys Leu<br>130                 135                 140                 145 | 490 |
| caa gat gct gta gga ccc cct aaa gta gat cct cac tca gtt aaa att<br>Gln Asp Ala Val Gly Pro Pro Lys Val Asp Pro His Ser Val Lys Ile<br>                  150                 155                 160 | 538 |
| aaa aaa atc aac aag aca gaa aca gac agc tat cta aac cat tgc tgc<br>Lys Lys Ile Asn Lys Thr Glu Thr Asp Ser Tyr Leu Asn His Cys Cys<br>                 165                 170                 175 | 586 |
| gga aca cga aga agt aaa act cta ggt cag agt ctc agg atc gtt ggt<br>Gly Thr Arg Arg Ser Lys Thr Leu Gly Gln Ser Leu Arg Ile Val Gly<br>180                 185                 190 | 634 |
| ggg aca gaa gta gaa gag ggt gaa tgg ccc tgg cag gct agc ctg cag<br>Gly Thr Glu Val Glu Glu Gly Glu Trp Pro Trp Gln Ala Ser Leu Gln<br>         195                   200              205 | 682 |
| tgg gat ggg agt cat cgc tgt gga gca acc tta att aat gcc aca tgg<br>Trp Asp Gly Ser His Arg Cys Gly Ala Thr Leu Ile Asn Ala Thr Trp<br>210                 215                 220                 225 | 730 |
| ctt gtg agt gct gct cac tgt ttt aca aca tat aag aac cct gcc aga<br>Leu Val Ser Ala Ala His Cys Phe Thr Thr Tyr Lys Asn Pro Ala Arg<br>                  230                 235                 240 | 778 |
| tgg act gct tcc ttt gga gta aca ata aaa cct tcg aaa atg aaa cgg<br>Trp Thr Ala Ser Phe Gly Val Thr Ile Lys Pro Ser Lys Met Lys Arg<br>         245                   250              255 | 826 |
| ggt ctc cgg aga ata att gtc cat gaa aaa tac aaa cac cca tca cat<br>Gly Leu Arg Arg Ile Ile Val His Glu Lys Tyr Lys His Pro Ser His<br>260                 265                 270 | 874 |
| gac tat gat att tct ctt gca gag ctt tct agc cct gtt ccc tac aca<br>Asp Tyr Asp Ile Ser Leu Ala Glu Leu Ser Ser Pro Val Pro Tyr Thr<br>         275                   280              285 | 922 |
| aat gca gta cat aga gtt tgt ctc cct gat gca tcc tat gag ttt caa<br>Asn Ala Val His Arg Val Cys Leu Pro Asp Ala Ser Tyr Glu Phe Gln<br>290                 295                 300                 305 | 970 |
| cca ggt gat gtg atg ttt gtg aca gga ttt gga gca ctg aaa aat gat<br>Pro Gly Asp Val Met Phe Val Thr Gly Phe Gly Ala Leu Lys Asn Asp<br>                  310                 315                 320 | 1018 |

-continued

```
ggt tac agt caa aat cat ctt cga caa gca cag gtg act ctc ata gac    1066
Gly Tyr Ser Gln Asn His Leu Arg Gln Ala Gln Val Thr Leu Ile Asp
        325                 330                 335 gct aca act tgc aat gaa cct caa gct tac aat gac gcc ata act cct    1114
Ala Thr Thr Cys Asn Glu Pro Gln Ala Tyr Asn Asp Ala Ile Thr Pro
340                 345                 350 aga atg tta tgt gct ggc tcc tta gaa gga aaa aca gat gca tgc cag    1162
Arg Met Leu Cys Ala Gly Ser Leu Glu Gly Lys Thr Asp Ala Cys Gln
            355                 360                 365 ggt gac tct gga gga cca ctg gtt agt tca gat gct aga gat atc tgg    1210
Gly Asp Ser Gly Gly Pro Leu Val Ser Ser Asp Ala Arg Asp Ile Trp
370                 375                 380                 385 tac ctt gct gga ata gtg agc tcg gga gat gaa tgt gcg aaa ccc aac    1258
Tyr Leu Ala Gly Ile Val Ser Ser Gly Asp Glu Cys Ala Lys Pro Asn
                390                 395                 400 aag cct ggt gtt tat act aga gtt acg gcc ttg cgg gac tgg att act    1306
Lys Pro Gly Val Tyr Thr Arg Val Thr Ala Leu Arg Asp Trp Ile Thr
                    405                 410                 415 tca aaa act ggt atc taa gagagaaaag cctcatggaa cagataacat           1354
Ser Lys Thr Gly Ile
            420 ttttttttgt tttttgggtg tggaggccat ttttagagat acagaattgg agaagacttg  1414 caaaacagct agatttgact gatctcaata aactgtttgc ttgatgcaaa aaaaaaa     1471

<210> SEQ ID NO 4
<211> LENGTH: 422
<212> TYPE: PRT
<213> ORGANISM: Homo sapiens

<400> SEQUENCE: 4

Met Tyr Arg Pro Asp Val Val Arg Ala Arg Lys Arg Val Cys Trp Glu
1               5                   10                  15

Pro Trp Val Ile Gly Leu Val Met Phe Ile Ser Leu Ile Val Leu Ala
            20                  25                  30

Val Cys Ile Gly Val Thr Val His Tyr Val Arg Tyr Asn Gln Lys Lys
        35                  40                  45

Thr Tyr Asn Tyr Tyr Ser Thr Leu Ser Phe Thr Thr Asp Lys Leu Tyr
    50                  55                  60

Ala Glu Phe Gly Arg Glu Ala Ser Asn Asn Phe Thr Glu Met Ser Gln
65                  70                  75                  80

Arg Leu Glu Ser Met Val Lys Asn Ala Phe Tyr Lys Ser Pro Leu Arg
                85                  90                  95

Glu Glu Phe Val Lys Ser Gln Val Ile Lys Phe Ser Gln Gln Lys His
            100                 105                 110

Gly Val Leu Ala His Met Leu Leu Ile Cys Arg Phe His Ser Thr Glu
        115                 120                 125

Asp Pro Glu Thr Val Asp Lys Ile Val Gln Leu Val Leu His Glu Lys
    130                 135                 140

Leu Gln Asp Ala Val Gly Pro Pro Lys Val Asp Pro His Ser Val Lys
145                 150                 155                 160

Ile Lys Lys Ile Asn Lys Thr Glu Thr Asp Ser Tyr Leu Asn His Cys
                165                 170                 175

Cys Gly Thr Arg Arg Ser Lys Thr Leu Gly Gln Ser Leu Arg Ile Val
            180                 185                 190

Gly Gly Thr Glu Val Glu Glu Gly Glu Trp Pro Trp Gln Ala Ser Leu
        195                 200                 205
```

```
Gln Trp Asp Gly Ser His Arg Cys Gly Ala Thr Leu Ile Asn Ala Thr
    210                 215                 220
Trp Leu Val Ser Ala Ala His Cys Phe Thr Thr Tyr Lys Asn Pro Ala
225                 230                 235                 240
Arg Trp Thr Ala Ser Phe Gly Val Thr Ile Lys Pro Ser Lys Met Lys
                245                 250                 255
Arg Gly Leu Arg Arg Ile Ile Val His Glu Lys Tyr Lys His Pro Ser
            260                 265                 270
His Asp Tyr Asp Ile Ser Leu Ala Glu Leu Ser Ser Pro Val Pro Tyr
        275                 280                 285
Thr Asn Ala Val His Arg Val Cys Leu Pro Asp Ala Ser Tyr Glu Phe
    290                 295                 300
Gln Pro Gly Asp Val Met Phe Val Thr Gly Phe Gly Ala Leu Lys Asn
305                 310                 315                 320
Asp Gly Tyr Ser Gln Asn His Leu Arg Gln Ala Gln Val Thr Leu Ile
                325                 330                 335
Asp Ala Thr Thr Cys Asn Glu Pro Gln Ala Tyr Asn Asp Ala Ile Thr
            340                 345                 350
Pro Arg Met Leu Cys Ala Gly Ser Leu Glu Gly Lys Thr Asp Ala Cys
        355                 360                 365
Gln Gly Asp Ser Gly Gly Pro Leu Val Ser Ser Asp Ala Arg Asp Ile
    370                 375                 380
Trp Tyr Leu Ala Gly Ile Val Ser Ser Gly Asp Glu Cys Ala Lys Pro
385                 390                 395                 400
Asn Lys Pro Gly Val Tyr Thr Arg Val Thr Ala Leu Arg Asp Trp Ile
                405                 410                 415
Thr Ser Lys Thr Gly Ile
                420

<210> SEQ ID NO 5
<211> LENGTH: 28
<212> TYPE: DNA
<213> ORGANISM: Homo sapiens

<400> SEQUENCE: 5
tgcatcaagc aaacagttta ttgagatc                                    28

<210> SEQ ID NO 6
<211> LENGTH: 25
<212> TYPE: DNA
<213> ORGANISM: Homo sapiens

<400> SEQUENCE: 6
cctgttccct acacaaathc agtac                                       25

<210> SEQ ID NO 7
<211> LENGTH: 28
<212> TYPE: DNA
<213> ORGANISM: Homo sapiens

<400> SEQUENCE: 7
tgacttggat gtagacctcg accttcac                                    28

<210> SEQ ID NO 8
<211> LENGTH: 22
<212> TYPE: DNA
<213> ORGANISM: Homo sapiens
```

```
<400> SEQUENCE: 8
ggaatagtga gctcgggaga tg                                              22

<210> SEQ ID NO 9
<211> LENGTH: 28
<212> TYPE: DNA
<213> ORGANISM: Homo sapiens

<400> SEQUENCE: 9
tcactgttca ttatgtgaga tataatca                                        28

<210> SEQ ID NO 10
<211> LENGTH: 27
<212> TYPE: DNA
<213> ORGANISM: Homo sapiens

<400> SEQUENCE: 10
caccattgat tcaagtctct ggctcat                                         27

<210> SEQ ID NO 11
<211> LENGTH: 17
<212> TYPE: DNA
<213> ORGANISM: Homo sapiens

<400> SEQUENCE: 11
gtaatgacca gtcaaca                                                    17

<210> SEQ ID NO 12
<211> LENGTH: 24
<212> TYPE: DNA
<213> ORGANISM: Homo sapiens

<400> SEQUENCE: 12
ccagcaagct tgcgaccttg acca                                            24

<210> SEQ ID NO 13
<211> LENGTH: 11
<212> TYPE: PRT
<213> ORGANISM: Artificial sequence
<220> FEATURE:
<223> OTHER INFORMATION: Substrate for DESC1 protease.

<400> SEQUENCE: 13

Pro Leu Ser Arg Thr Leu Ser Val Ala Ala Lys
1               5                   10
```